United States Patent
Bell et al.

(10) Patent No.: US 6,355,271 B1
(45) Date of Patent: Mar. 12, 2002

(54) THERAPEUTIC CALCIUM PHOSPHATE PARTICLES AND METHODS OF MANUFACTURE AND USE

(75) Inventors: Steve J. D. Bell, Marietta; Tulin Morco, Decatur; Qing He, Atlanta, all of GA (US)

(73) Assignee: Biosante Pharmaceuticals, Inc., Smyrna, GA (US)

(*) Notice: Subject to any disclaimer, the term of this patent is extended or adjusted under 35 U.S.C. 154(b) by 0 days.

(21) Appl. No.: 09/496,771

(22) Filed: Feb. 3, 2000

Related U.S. Application Data

(60) Provisional application No. 60/118,356, filed on Feb. 3, 1999, provisional application No. 60/118,364, filed on Feb. 3, 1999, and provisional application No. 60/118,355, filed on Feb. 3, 1999.

(51) Int. Cl.$^7$ ................................................. A61K 9/14
(52) U.S. Cl. ..................... 424/489; 424/491; 424/493; 424/499; 424/278.1; 514/770
(58) Field of Search ......................... 424/184.1, 204.1, 424/490, 493, 489, 453, 278.1, 499, 491; 514/2, 770, 951, 970

(56) References Cited

U.S. PATENT DOCUMENTS

| | | |
|---|---|---|
| 3,925,545 A | 12/1975 | Relyveld |
| 4,016,252 A | 4/1977 | Relyveld |
| 4,350,686 A | 9/1982 | Relyveld et al. |
| 4,500,512 A | 2/1985 | Barme |
| 4,552,756 A | 11/1985 | Relyveld et al. |
| 5,178,882 A | 1/1993 | Kossovsky et al. |
| 5,219,577 A | 6/1993 | Kossovsky et al. |
| 5,306,508 A | 4/1994 | Kossovsky et al. |
| 5,334,394 A | 8/1994 | Kossovsky et al. |
| 5,364,838 A | 11/1994 | Rubsamen |
| 5,460,830 A | 10/1995 | Kossovsky et al. |
| 5,460,831 A | 10/1995 | Kossovsky et al. |
| 5,462,750 A | 10/1995 | Kossovsky et al. |
| 5,462,751 A | 10/1995 | Kossovsky et al. |
| 5,464,634 A | 11/1995 | Kossovsky et al. |
| 5,506,203 A | 4/1996 | Backstrom et al. |
| 5,549,973 A | 8/1996 | Majetich et al. |
| 5,580,859 A | 12/1996 | Felgner et al. |
| 5,593,875 A | 1/1997 | Wurm et al. |
| 5,595,762 A | 1/1997 | Derrieu et al. |
| 5,620,896 A | 4/1997 | Herrmann et al. |
| 5,629,021 A | 5/1997 | Wright |
| 5,641,515 A | 6/1997 | Ramtoola |
| 5,648,097 A | 7/1997 | Nuwayser |
| 5,695,617 A | 12/1997 | Gravier et al. |
| 5,747,001 A | 5/1998 | Wiedmann et al. |
| 5,785,975 A | 7/1998 | Parikh |
| 5,827,822 A | 10/1998 | Floc'h et al. |
| 5,866,553 A | 2/1999 | Donnelly et al. |
| 5,891,420 A | 4/1999 | Cutie |
| 5,898,028 A | 4/1999 | Jensen et al. |
| 5,902,789 A | 5/1999 | Stolz |

FOREIGN PATENT DOCUMENTS

| | | |
|---|---|---|
| FR | 7212036 | 12/1973 |
| FR | 7924948 | 4/1981 |
| GB | 1422973 | 1/1976 |
| WO | WO 90/11092 | 10/1990 |
| WO | WO 93/17706 | 9/1993 |
| WO | WO 93/24640 | 12/1993 |
| WO | WO98/35562 | 8/1998 |
| WO | WO00/15194 | 3/2000 |
| WO | WO 00/46147 | 8/2000 |

OTHER PUBLICATIONS

Academic Press Dictionary of Science and Technology. http://www.harcourt.com/dictionary/def/2/2/3/1/2231200.html, Nov. 2000.*

Abstracts of Papers Presented at the 1992 meeting on Modern Approaches to New Vaccines, Including Prevention of AIDS, Cold Spring Harbor), *Vaccine* 11: 92 (1993).

Aldovini and R. A. Young, "Humoral and cell–mediated immune responses to live recombinant BCG–HIV vaccines," *Nature* 351: 479–482 (1991).

Ascadi et al., "Human dystrophin expression in mdx mice after intramuscular injection of DNA constructs," *Nature* 352: 815–818 (1991).

Bartus et al., "Sustained Delivery of Proteins for Novel Therapeutic Products," *Science,* 281(5380): 1161–1162 (1998).

Bastin, et al., "Use of Synthetic Peptides of Influenza Nucleoprotein to Define Epitopes Recognized by Class I–Restricted Cytotoxic T Lymphocytes," *J. Exp. Med.,* 165(4): 1508–1523 (1987).

Benvenisty, N., and Reshef, L. *PNAS* 83, 9551–9555, (1986).

Bennink and J. W. Yewdell, "Recombinant Vaccinia Viruses as Vectors for Studying T Lymphocyte Specificity and Function," *Curr. Top. Microbiol. Immunol.,* 163:153–184 (1990).

(List continued on next page.)

*Primary Examiner*—Donna C. Wortman
*Assistant Examiner*—Robert A. Zeman
(74) *Attorney, Agent, or Firm*—Bruce D. Gray; Kristin D. Mallatt; Kilpatrick Stockton LLP

(57) ABSTRACT

Novel calcium phosphate core particles, methods of making them, and methods of using them as vaccine adjuvants, as cores, as carriers of biologically active material, and as controlled release matrices for biologically active material are disclosed. The core particles may have a surface modifying agent and/or biologically active material, such as antigenic material or natural immunoenhancing factor, polynucleotide material, or therapeutic proteins or peptides, partially coating the particle or impregnated therein. The core particles have a diameter between about 300 nm and about 4000 nm, more particularly between about 300 nm and about 2000 nm, and even more particularly between about 300 nm and about 1000 nm, are substantially spherical in shape, and have a substantially smooth surface.

3 Claims, 14 Drawing Sheets

OTHER PUBLICATIONS

Figure 1A:
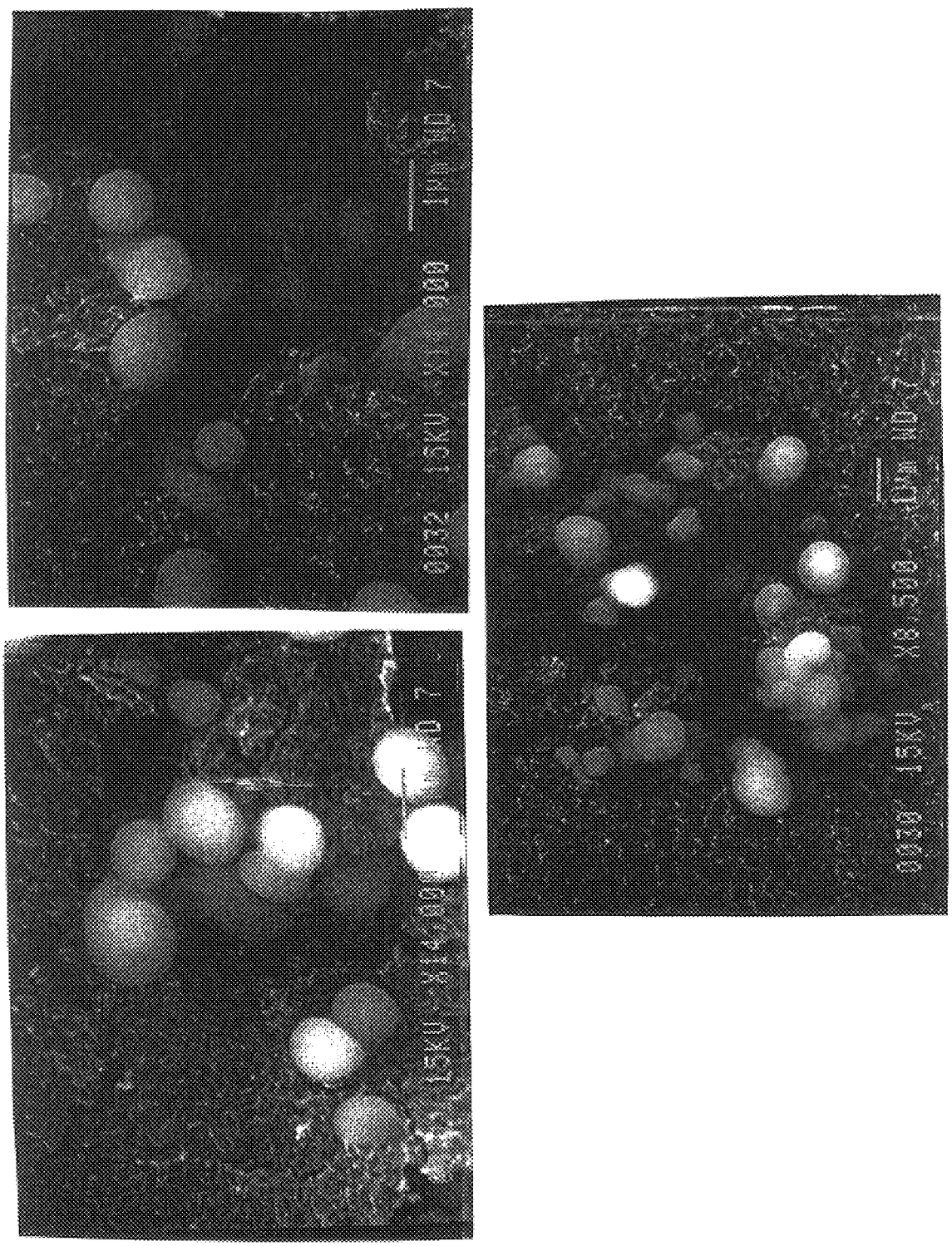

Carbone and Bevan, "Induction of Ovalbumin–specific cytotoxic T cells by in vivo peptide immunization," *J. Exp. Med.,* 169(1): 603–612 (1989).

Collins et al., "Processing of exogenous liposome–encapsulated antigens in vivo generates class I MCH–restricted T cell responses," *J. Immunol.,* 148(11): 3336–3341 (1992).

Cooney et al., "Safety of and immunological response to a recombinant vaccinia virus vaccine expressing HIV envelope glycoprotein," *Lancet,* 337: 567–572 (1991).

Cox et al., "Bovine Herpesvirus 1: Immune Responses in Mice and Cattle Injected with Plasmid DNA," 1993, *J. Virol.,* 67(9): 5664–5667.

Deres, et al., "In vivo priming of virus–specific cytotoxic T lymphocytes with synthetic lipoprotein vaccine," *Nature,* 342: 561–564 (1989).

Donnelly et al., "DNA Vaccines," *Annu. Rev. Immunol.,* 15: 617–648 (1997).

Edgington, "Turning On Tumor–Fighting T–Cells," *Biotechnology,* 11:1117–1119 (1993).

Edwards et al., *Science,* 276:1868 (1997) *.

Friedman, T., "Progress toward human gene therapy," *Science,* 244, 1275–1281 (1989).

Furth et al., "Gene Transfer into Somatic Tissues by Jet Injection," *Analytical Biochemistry,* 205(2): 365–368, (1992).

Gardner et al., "Cell–mediated cytotoxicity against ectromelia virus–infected target cells," *Eur. J. Immunol.,* 4: 68–72 (1974).

Goto et al., "Local tissue irritating effects and adjuvant activities of calcium phosphate and aluminum hydroxide with different physical properties," *Vaccine,* 15(12/13):1364–1371 (1997).

Hahn et al., "Infectious Sindbis virus transient expression vectors for studying antigen processing and presentation," *Proc. Natl. Acad. Sci.* (USA) 89: 2679–2683 (1992).

Hansen et al., *FEBS Lett.* 290, 73 (1991).

Jiao et al., *Hum. Gene Therapy* 3, 21 (1992) *.

Kato et al., "Relationship between Hemolytic Activity and Adsorption Capacity of Aluminum Hydroxide and Calcium Phosphate as Immunological Adjuvants for Biologicals," *Microbiol. Immunol.,* 38(7): 543–548 (1994).

Kitsis et al., "Hormonal modulation of a gene injected into rat heart in vivo," *Proc. Natl. Acad. Sci.* (USA) 88: 4138–4142 (1991).

Lin et al., "Expression of Recombinant Genes in Myocardium In Vivo after Direct Injection of DNA," *Circulation* 82(6): 2217–2221 (1990).

Lin and Askonas, "Biological properties of an influenza A virus–specific killer T cell clone," J. Exp. Med. 154(1): 225–234 (1981).

Maniatis, et al., *Molecular Cloning,* Cold Spring Harbor Laboratory Press, New York, 1.0–19.0 (1989). *.

Mascola et al., "Surveillance of Listeriosis in Los Angeles County, 1985–1986," *Arch. Intern. Med.,* 149(7): 1569–1572 (1989).

McMichael et al., "Cytotoxic T–Cell Immunity to Influenza," *New Engl. J. Med.,* 309(1): 13–17 (1983).

McMichael et al., "Recognition of Influenza A virus Nucleoprotein by human cytotoxic T lymphocytes," *J. Gen. Virol.,* 67: 719–726 (1986).

Miller, "Retroviral Vectors," *Curr. Top. Microbiol. Immunol.,* 158, 3–24 (1992).

Montgomery, D. L. et al., 1993, *Cell Biol.,* 12, pp. 777–783. *.

Redfield et al., "Disseminated Vaccinia in a Military Recruit with Human Immunodeficiency Virus (HIV) Disease," *New Engl. J. Med.,* 316(11): 673–676 (1987).

Robinson et al., "Protection against a lethal influenza virus challenge by immunization with a haemagglutinin–expressing plasmid DNA," *Vaccine* 11(9): 957–960 (1993).

Sato et al., "Immunostimulatory DNA Sequences Necessary for Effective Intradermal Gene Immunization," *Science* 273: 352–354 (1996).

Schafer et al., "Induction of a cellular immune response to a foreign antigen by a recombinant *Listeria monocytogenes* vaccine," *J. Immunol.,* 149(1):53–59 (1992).

Service, *Science* 277:5330 (1997). *.

Stover et al., "New use of BCG for recombinant vaccines," *Nature* 351: 456–460 (1991).

Takahashi et al., "Induction of CD8 cytotoxic T cells by immunization with purified HIV–1 envelope protein in ISCOMs," *Nature,* 344: 873–875 (1990).

Tang et al., "Genetic immunization is a simple method for eliciting an immune response," *Nature,* 356: 152–154 (1992).

Taylor and Askonas, "Influenza nucleoprotein–specific cytotoxic T–cell clones are protective in vivo," *Immunol.,* 58(1): 417–420 (1986).

Townsend, "Antigen recognition by class I–restricted T lymphocytes," *Annu. Rev. Immunol.,* 7: 601–624 (1989).

Townsend et al., "The Epitopes of Infulenza Nucleoprotein Recognized by Cytotoxic T Lymphocytes Can Be Defined with Short Synthetic Peptides," *Cell* 44: 959–968 (1986).

Ulmer, J. B. et al., "Heterologous Protection Against Influenza by Injection of DNA Encoding a Viral Protein," *Science,* 259: 1745–1749 (1993).

Wang et al., "Gene inoculation generates immune responses against human immunodeficiency virus type I," *P.N.A.S.* USA 90: 4156–4160 (May, 1993).

Wang, et al., "Enhanced type I immune response to a hepatitis B DNA vaccine by formulation with calcium– or aluminum phosphate," *Vaccine,* 18: 1227–1235 (2000).

Weiner et al., "Immunostimulatory oligodeoxynucleotides containing the CpG motif are effective as immune adjuvants in tumor antigen immunization," *PNAS* (*USA*) 94(19): 10833–10837 (1997).

Wolff et al., "Long–term persistence of plasmid DNA and foreign gene expression in mouse muscle," *Human Mol. Genet.* 1(6): 363–369 (1992).

Wolff et al., "Direct Gene Transfer into Mouse Muscle in Vivo," *Science* 247: 1465–1468 (1990).

Yap and Ada, "Transfer of specific cytotoxic T lymphocytes protects mice inoculated with influenza virus," *Nature,* 273: 238–239 (1978).

Yewdell et al., "Influenza A virus nucleoprotein is a major target antigen for cross–reactive anti–influenza A virus cytotoxic T lymphocytes," *Proc. Natl. Acad. Sci.* (USA) 82: 1785–1789 (1985).

Zhu et al., "Systemic Gene Expression After Intravenous DNA Delivery into Adult Mice," *Science* 261: 209–211 (1993).

* cited by examiner

FIGURE 7A
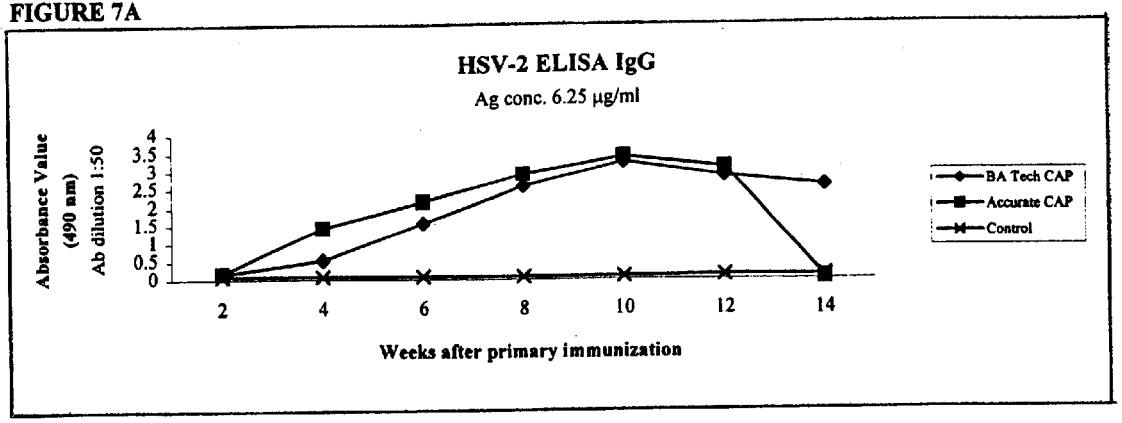
FIGURE 7B
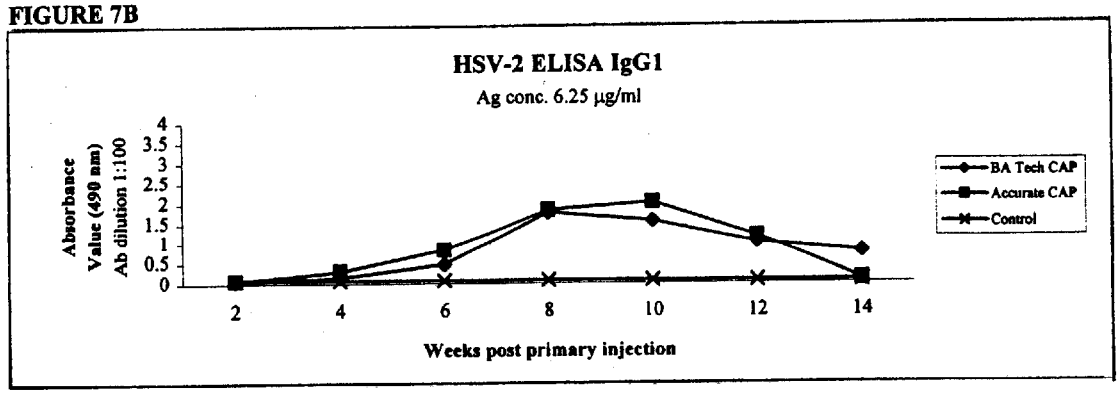
FIGURE 7C
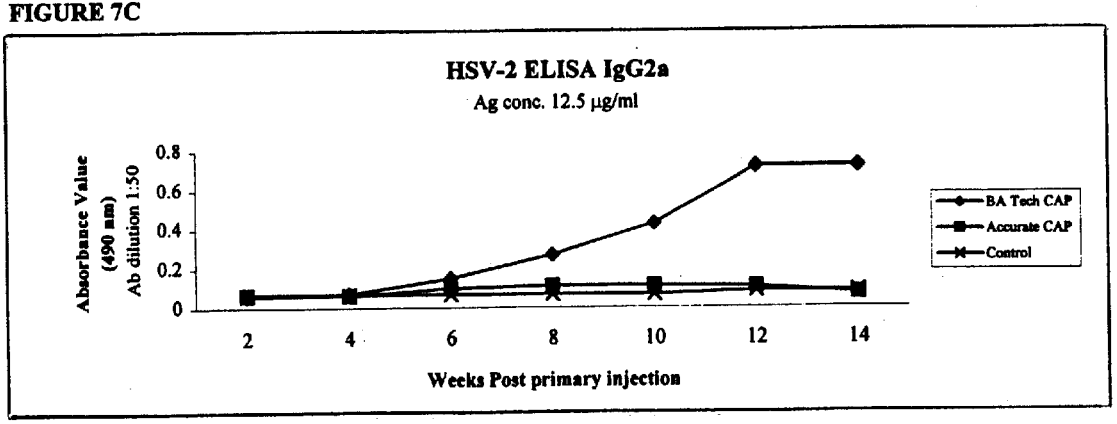
FIGURE 7

9A

9B

9C

9D

11A

11B

11C

11D

THERAPEUTIC CALCIUM PHOSPHATE PARTICLES AND METHODS OF MANUFACTURE AND USE

This application claims benefit of the filing dates of U.S. Provisional Application Ser. Nos. 60/118,356; 60/118,364; and 60/118,355, all filed Feb. 3, 1999, the entire contents of each of which are hereby incorporated by reference.

BACKGROUND OF INVENTION

1. Field of the Invention

The present invention relates to novel calcium phosphate core particles, to methods of making them, and to methods of using them as vaccine adjuvants, as cores or carriers for biologically active material, and as controlled release matrices for biologically active material.

2. Description of Related Art

Nanometer scale particles have been proposed for use as carrier particles, as supports for biologically active molecules, such as proteins, and as decoy viruses. See U.S. Pat. Nos. 5,178,882; 5,219,577; 5,306,508; 5,334,394; 5,460,830; 5,460,831; 5,462,750; and 5,464,634, the entire contents of each of which are hereby incorporated by reference.

The particles disclosed in the above-referenced patents, however, are generally extremely small, in the 10–200 nm size range. Particles of this size are difficult to make with any degree of consistency, and their morphology is not described in any detail. None of these patents disclose the use of nanoparticles as sustained release matrices. Furthermore, these patents do not disclose the use of calcium phosphate particles as either (1) adjuvants for vaccines or viral decoys, or (2) controlled release matrices for delivery of pharmaceuticals or immunogenic materials.

There has been a suggestion in the literature to use calcium phosphate particles as vaccine adjuvants, but calcium phosphate particles have generally been considered an unsuitable alternative to other adjuvants due to inferior adjuvanting activity. See, e.g., Goto et al., *Vaccine*, vol. 15, no. 12/13 (1997). Moreover, the calcium phosphate evaluated was typically microparticulate (>1000 nm diameter) and possessed a rough and oblong morphology, in contrast to the core particles of the present invention.

Therefore, an important need remains for calcium phosphate core particles useful as core materials or carriers for biologically active moieties which can be produced simply and consistently. A further need remains for calcium phosphate core particles that can be effectively used as adjuvants for vaccines, as cores or carriers for biologically active molecules, and as controlled release matrices.

There is also a need for calcium phosphate core particles that can be effectively used as supports and matrices for sustained release of polynucelotide material (DNA or RNA) encoding immunogenic polypeptides. Traditional vaccination involves exposing a potential host to attenuated or killed pathogens, or immunogenic components thereof (e.g., proteins or glycoproteins). The basic strategy has changed little since the development of the first smallpox vaccine nearly a century ago, although modern developments permit genetic engineering of recombinant protein vaccines. However, traditional vaccine methodologies may be undesirable as a result of their expense, instability, poor immunogenicity, limited heterogeneity and potential infectivity.

Polynucleotide vaccination presents a different vaccine methodology, whereby polynucelotide material, such as DNA or RNA, encoding an immunogenic polypeptide is delivered intracellularly to a potential host. The genetic material is taken up and expressed by these cells, leading to both a humoral and a cell-mediated immune response. It is not entirely clear whether DNA vaccines function as a result of integration or simply long-term episomal maintenance.

Polynucleotide vaccination provides numerous advantages over traditional vaccination. Polynucleotide vaccines eliminate the risk of infection associated with live attenuated viruses, yet advantageously induce both humoral and cell-mediated responses. Polynucleotide vaccines further provide prolonged immunogen expression, generating significant immunological memory and eliminating the need for multiple inoculations. Polynucleotide vaccines are very stable, permitting prolonged storage, transport and distribution under variable conditions. As a further advantage, a single polynucleotide vaccine may be engineered to provide multiple immunogenic polypeptides. Thus, a single DNA vaccine can be used to immunize against multiple pathogens, or multiple strains of the same pathogen. Finally, polynucleotide vaccines are much simpler and less expensive to manufacture than traditional vaccines.

Polynucleotide vaccines may take various forms. The genetic material can be provided, for example, in combination with adjuvants capable of stimulating the immune response. Administration of the DNA or RNA coated onto microscopic beads has been suggested. See J. J. Donnelly et al., *Annu. Rev. Immunol.* 15, 617 (1997). Various routes of administration are also possible, and may include, for example, intravenous, subcutaneous and intramuscular administration.

A desirable immune response to an immunogenic polypeptide is two-fold, involving both humoral and cellular-mediated immunity. The humoral component involves stimulation of B cells to product antibodies capable of recognizing extracellular pathogens, while the cell-mediated component involves T lymphocytes capable of recognizing intracellular pathogens. Cytotoxic T-lymphocytes (CTLs) play an important role in the latter, by lysing virally-infected or bacterially-infected cells. Specifically, CTLs possess receptors capable of recognizing foreign peptides associated with MHC class I and/or class II molecules. These peptides can be derived from endogenously synthesized foreign proteins, regardless of the protein's location or function within the pathogen. Thus, CTLs can recognize epitopes derived from conserved internal viral proteins (J. W. Yewdell et al., *Proc. Natl. Acad. Sci.* (USA) 82, 1785 (1985); A. R. M. Towsend, et al., *Cell* 44, 959 (1986); A. J., McMichael et al., *J. Gen. Virol.* 67, 719 (1986); A. R. M. Towsend and H., *Annu. Rev. Immunol.* 7, 601 (1989)) and may therefore permit heterologous protection against viruses with multiple serotypes or high mutation rates. Polynucleotide vaccination can stimulate both forms of immune response, and thus is very desirable.

Efforts to use polynucleotide vaccination have focused on the use of viral vectors to deliver polynucleotides to host cells. J. R. Bennink et al., 311, 578 (1984); J. R. Bennink and J. W. Yewdell, *Curr. Top. Microhiol. Immunol.* 163, 153 (1990); C. K. Stover et al., *Nature* 351, 456 (1991); A. Aldovini and R. A. Young, *Nature* 351, 479 (1991); R. Schafer et al., *J. Immunol.* 149, 53 (1992); C. S. Hahn et al., *Proc. Natl. Acad. Sci.* (USA) 89, 2679 (1992). However, this approach may be undesirable for several reasons. Retroviral vectors, for example, have restrictions on the size and structure of polypeptides that can be expressed as fusion proteins while maintaining the ability of the recombinant virus to replicate (A.D. Miller, *Curr. Top. Microbiol. Immu-* nol. 158, 1 (1992). The effectiveness of vectors such as vaccinia for subsequent immunizations may be compromised by immune responses against vaccinia (E. L. Cooney et al., *Lancet* 337, 567 (1991)). Also, viral vectors and modified pathogens have inherent risks that may hinder their use in humans (R. R. Redfield et al., *New Engl. J Med.* 316, 673 (1987); L. Mascola et al., *Arch. Intern. Med.* 149, 1569 (1989)). For example, in live vector approaches, highly immunogenic vectors also tend to be highly pathogenic.

Alternative gene delivery methods have also been explored. Benvenisty, N., and Reshef, L. (*PNAS* 83, 9551–9555, (1986)) showed that $CaCl_2$ precipitated DNA could be expressed in mice. Plasmid vectors have also been used to produce expression in mouse muscle cells (J. A. Wolff et al., *Science* 247, 1465 (1990); G. Ascadi et al., *Nature* 352, 815 (1991)). The plasmids were shown to be maintained episomally and did not replicate. Subsequently, persistent expression has been observed after i.m. injection in skeletal muscle of rats, fish and primates, and cardiac muscle of rats (H. Lin et al., *Circulation* 82, 2217 (1990); R. N. Kitsis et al., *Proc. Natl. Acad. Sci.* (USA) 88, 4138 (1991); E. Hansen et al., *FEBS Lett.* 290, 73 (1991); S. Jiao et al., *Hum. Gene Therapy* 3, 21 (1992); J. A. Wolff et al., *Human Mol. Genet.* 1, 363 (1992)). WO 90/11092 (Oct. 4, 1990) reported the use of naked polynucleotides to vaccinate vertebrates.

Various routes of administration have been found to be suitable for vaccination using polynucleotide vaccines. Intramuscular administration is thought to be particularly desirable, given the proportionally large muscle mass and its direct accessibility through the skin. See U.S. Pat. No. 5,580,859. Tang et al., (*Nature,* 356, 152–154 (1992)) disclosed that introduction of gold microprojectiles coated with DNA encoding bovine growth hormone (BGH) into the skin of mice resulted in production of anti-BGH antibodies in the mice. Furth et al., (*Analytical Biochemistry,* 205, 365–368, (1992)) showed that a jet injector could be used to transfect skin, muscle, fat, and mammary tissues of living animals. WO 93/17706 describes a vaccination method wherein carrier particles are coated with a gene construct and then accelerated into a potential host. Intravenous injection of a DNA:cationic liposome complex in mice has also been reported (Zhu et al., *Science* 261, 209–211 (Jul. 9, 1993); see also WO 93/24640). Methods for introducing nucleic acids have been reviewed (Friedman, T., *Science,* 244, 1275–1281 (1989)), see also Robinson et al., (Abstracts of Papers Presented at the 1992 meeting on Modern Approaches to New Vaccines, Including Prevention of AIDS, Cold Spring Harbor, p 92; Vaccine 11, 957 (1993)), where the intramuscular, intra-venous, and intra-peritoneal administration of avian influenza DNA into chickens was alleged to have provided protection against lethal challenge.

Reports suggest that polynucleotide vaccination has provided effective protective immunity in various animal models. The immunization of mice against influenza by the injection of plasmids encoding influenza A hemagglutinin has been reported (Montgomery, D. L. et al., 1993, *Cell Biol.,* 12, pp. 777–783), or nucleoprotein (Montgomery, D. L. et al., supra; Ulmer, J. B. et al., 1993, *Science,* 259, pp. 1745–1749). The first use of DNA immunization for a herpes virus has been reported (Cox et al., 1993, *J. Virol.,* 67, pp. 5664–5667). Injection of a plasmid encoding bovine herpes virus 1 (BHV-1) glycoprotein g IV gave rise to anti-g IV antibodies in mice and calves. Upon intranasal challenge with BHV-1, immunized calves showed reduced symptoms and shed substantially less virus than controls. Wang et al., (*P.N.A.S.* USA 90, 4156–4160 (May, 1993)) reported on elicitation of immune responses in mice against HIV by intramuscular inoculation with a cloned, genomic (unspliced) HIV gene. However, the level of immune responses achieved was very low, and the system utilized portions of the mouse mammary tumor virus (MMTV) long terminal repeat (LTR) promoter and portions of the simian virus 40 (SV40) promoter and terminator. SV40 is known to transform cells, possibly through integration into host cellular DNA. Thus, the system described by Wang et al., may be inappropriate for administration to humans.

It has been suggested to use calcium phosphate particles as agents for transfection of therapeutic polynucleotides in gene therapy. See U.S. Pat. No. 5,460,831. DNA or RNA is attached to the particulate core and delivered to a target cell, resulting in expression of therapeutic proteins. However, this patent does not suggest the use of calcium phosphate particles as supports for DNA or RNA vaccines. To the contrary, this patent indicates that the stimulation of an immunological response during transfection is to be avoided. This patent also fails to suggest the use of calcium phosphate particles as controlled release matrices for genetic material.

There is also a need for calcium phosphate core particles that can be used effectively used as an inhalable aerosol delivery system for the delivery of therapeutic proteins or peptide agents, and in particular, for delivery of insulin and other hormones. For a number of therapeutic agents, delivery of the agent to a patient in need thereof can be difficult. This is particularly true with proteins and peptides, which are difficult or impossible to administer orally, since they are easily digested or hydrolyzed by the enzymes and other components of gastric juices and other fluids secreted by the digestive tract. Injection is often the primary alternative administration method, but is unpleasant, expensive and is not well tolerated by patients requiring treatment for chronic illnesses. In particular, patients who are administered drugs on an out-patient basis, or who self-administer, are more likely to fail to comply with the required administration schedule. A particular group of patients of this type are those suffering from diabetes, who frequently must inject themselves with insulin in order to maintain appropriate blood glucose levels.

Recently, alternative methods of administration therapeutic agents have been sought, in particular, administration by inhalation of an aerosol containing the therapeutic agent. The lungs can be used effectively to get the therapeutic agent into the bloodstream because they have a very large surface area of very thin tissue. As a result, for some therapeutic agents and delivery systems, the level of agent in the blood can rise as fast as, or faster than, that obtained when the agent is administered by injection beneath the skin. Moreover, the thin lung tissue allows the passage of proteins and peptides into the blood stream without exposing them to the type or level of proteases encountered during oral administration.

Aerosols containing the therapeutic agent as fine, suspended mists of particles in both liquid and solid form have been investigated. However, preparation of suitable inhalable aerosols can be difficult for therapeutic agents where the blood level of the agent is critical, e.g., with insulin, because the amount of aerosol delivered to the deep lung tissue can be substantially variable, leading to inconsistent dosages of the drug to the patient.

As a result of this need to provide a reliable inhalable aerosol delivery system, various attempts have been made to develop small, solid particles for the delivery of therapeutic agents via inhalation. For example, an inhalable form of insulin is reportedly under development wherein the insulin is combined with sugar particles of a particular size to make an ultrafine powder that is delivered when it is forced through an inhaler nozzle by a blast of compressed air. See R. F. Service, Science 277:5330 (1997). Another inhalable form of insulin involves relatively large (diameters >5 µm), porous polymer particles (50:50 poly(lactic acid-co-glycolic acid) of low density ($\rho$<~0.4 g/cm$^3$) that encapsulate insulin. The particles are believed to penetrate deep into the lung tissue as the result of their low density, yet avoid phagocytosis when in the tissue as the result of their large size. See D. E. Edwards et al., Science, 276:1868 (1997).

Despite these attempts, there remains a need for an inhalable aerosol delivery system that effectively provides consistent, reliable, therapeutic blood levels of protein or peptide therapeutic agents, and in particular, of insulin and other hormones. It is particularly desirable that any carrier material be very small and easily biodegradable, in order to avoid complications resulting from inhalation of particulates.

SUMMARY OF THE INVENTION

The present invention relates to novel calcium phosphate ("CAP") core particles, to methods of making them, and to methods of using them as vaccine adjuvants, as cores or carriers for biologically active material, and as controlled release matrices for biologically active material. More particularly, the invention relates to the core particles having a diameter between about 300 nm and about 4000 nm, more particularly between about 300 nm and about 1000 nm, and having a substantially spherical shape and a substantially smooth surface.

The present invention also relates to the novel calcium phosphate core particles having a material coated on the surface of the core particles, and/or dispersed or impregnated within the core particles, to methods of making them, and to methods of using them. Non-limiting examples of a suitable material to be at least partially coated on the surface of the core particle or impregnated therein include one or more of the following: antigenic material, natural immunoenhancing factors, polynucleotide material encoding immunogenic polypeptides, or therapeutic proteins or peptides.

The present invention also relates to combinations of this novel core particle having at least a partial coating of a surface modifying agent or a surface modifying agent impregnated therein or both. If one or more of the above-mentioned materials (e.g., antigenic material, natural immunoenhancing factors, polynucleotide material, or therapeutic proteins or peptides) is at least partially coated on the particle, the material may be optionally attached to the particle by the surface modifying agent, which acts as a biological 'glue,' such as cellobiose or polyethylene glycol (PEG).

The invention also relates to combinations of this novel core particle with antigenic material, natural immunoenhancing factors, polynucleotide material, or therapeutic proteins or peptides integrated into the core particle, forming a controlled release matrix that releases the material into a patient over time.

One embodiment of the present invention relates to methods of adjuvanting vaccines, whether live, killed, attenuated, a decoy virus, or made from core particles at least partially coated with microbial antigenic material, or combinations thereof, by administering the novel uncoated core particles or core particles coated with natural immunoenhancing factor to a patient in need of vaccination either alone or in combination or conjunction with administration of the vaccine. The core particles are sufficiently small to be easily transportable to various tissues throughout the body, and are biodegradable as well.

The invention also relates to methods of vaccinating patients in need thereof by administering the novel core particle in combination or in conjunction with an antigenic material or natural immunoenhancing factor, wherein the antigenic material or natural immunoenhancing factor is at least partially coated on the core particle and/or integrated therein, as described in more detail below. The calcium phosphate core particles of this embodiment significantly increase the efficacy of the vaccines with which they are administered, by enhancing the magnitudes, qualities, and/or durations of the immune responses.

In another embodiment, the invention also relates to a polynucleotide vaccine having polynucleotide material at least partially coated on the novel core particle and/or impregnated therein. Contrary to conventional wisdom, the present inventors have discovered novel calcium phosphate particles that can be effectively used as supports and matrices for sustained release of DNA or RNA encoding immunogenic polypeptides. The present inventors have discovered that a DNA or RNA vaccine can be prepared that uses a biodegradable matrix of calcium phosphate, that functions as a sustained release composition, conferring long lasting immunity, and that is, in effect, self-adjuvanting. The primary intent is that the respective protein translation products produced by the present invention would immediately be available both intracellularly and extracellularly, to elicit enhanced humoral and cellular immune responses.

When administered as a polynucleotide vaccine, the calcium phosphate in the core particles of the present invention biodegrades, releasing into the surrounding tissue polynucleotide material (DNA or RNA) coding for immunogenic polypeptides. Without wishing to be bound to any theory, it is believed that cells in the patient take up the DNA or RNA and express it as immunogenic proteins, which are then presented to B cells and T cells of the immune system, resulting in both a humoral and cell-mediated response similar to that obtained using live attenuated virus, but without the risks of pathogenicity and without the loss of immunogenicity associated with live virus. When the DNA or RNA is impregnated or dispersed within the calcium phosphate core particle, the gradual release of genetic material by the dissolution of the calcium phosphate matrix provides longer lasting immune responses than does administration of a conventional DNA or RNA vaccine.

In addition, while not wishing to be bound by any theory, it is believed that the presence of calcium phosphate core particles enhances the immune response to the antigenic proteins produced by the cells that take up and express the DNA or RNA, further multiplying the protective effect of the vaccine. The size of the core particles of the invention allows them to migrate through the body as the calcium phosphate gradually degrades, thereby transporting the DNA/RNA to different tissues in the body, and enlisting large numbers of different tissues at different locations in the production of antigenic proteins.

In still a further embodiment, this invention relates to an inhalable, aerosolizable therapeutic composition, having a therapeutic protein or peptide material either at least partially coated on the novel calcium phosphate core particle and/or impregnated therein. The surface of the core particle may be at least partially coated with a surface modifying agent that bonds proteins or peptides to the core particle without denaturing the proteins or peptides. A therapeutic protein or peptide, in particular a hormone such as insulin, is disposed on the resulting coated core particle.

The present invention also relates to methods of treating medical conditions resulting from protein or peptide deficiencies by administering effective amounts of the core particles of this particular embodiment to a patient in need thereof via inhalation into the lungs. The therapeutic compositions of the present invention are highly stable, and exhibit enhanced bioavailability. These therapeutic compositions also exhibit preferable biodynamics including controlled release of therapeutic polypeptides or proteins.

The present invention also relates to methods of preparing the novel calcium phosphate core particles described above, such as the core particles for use individually, the core particles having material at least partially coated on the surface, and the core particles having material impregnated therein.

The above discussed and many other features and attendant advantages of the present invention are detailed below.

BRIEF DESCRIPTION OF THE FIGURES

FIGS. 1A and 1B are photomicrographs of the calcium phosphate core particles according to one embodiment of the present invention.

FIG. 2 presents a series of graphs showing the ELISA results for a calcium phosphate—tuberculosis antigen conjugate according to one embodiment of the present invention. FIG. 2A shows ELISA results three weeks after primary vaccination. FIG. 2B shows ELISA results seven weeks after primary vaccination. FIG. 2C shows ELISA results three months after primary vaccination. FIG. 2D shows ELISA results five months after primary vaccination.

FIG. 3 presents a series of graphs showing the ELISA results for a calcium phosphate—influenza antigen conjugate according to one embodiment of the present invention. FIG. 3A shows ELISA results three weeks after primary vaccination. FIG. 3B shows ELISA results eight weeks after primary vaccination. FIG. 3C shows ELISA results ten weeks after primary vaccination.

FIG. 4 presents a series of graphs showing ELISA results for a calcium phosphate—herpes simplex 2 antigen conjugate according to one embodiment of the present invention. FIG. 4A shows ELISA results two weeks after primary vaccination. FIG. 4B shows ELISA results four weeks after primary vaccination. FIG. 4C shows ELISA results five weeks after primary vaccination.

FIG. 5 is a graph showing ELISA and neutralization assay results for a calcium phosphate—herpes simplex 2 antigen conjugate according to one embodiment of the present invention.

FIG. 6 is a graph showing ELISA results for a calcium phosphate—human immunodeficiency virus antigen conjugate according to one embodiment of the present invention.

FIG. 7 presents a series of graphs showing ELISA results for a calcium phosphate—herpes simplex 2 antigen conjugate according to one embodiment of the present invention compared to the ELISA results for a calcium phosphate—herpes simplex 2 antigen conjugate made from Accurate CAP, which is produced by Superfos Biosector a/s. FIG. 7A shows ELISA results with an IgG antibody titer. FIG. 7B shows ELISA results with an IgG1 antibody titer. FIG. 7C shows ELISA results with an IgG2a antibody titer.

FIG. 8 presents a series of graphs showing the ELISA results for a calcium phosphate—Epstein-Barr virus antigen conjugate according to one embodiment of the present invention. FIG. 8A shows ELISA results with an IgG antibody titer. FIG. 8B shows ELISA results with an IgG2a antibody titer. FIG. 8C shows ELISA results with an IgG1 antibody titer. FIG. 8D shows ELISA results with an IgE antibody titer.

FIG. 9 presents a series of graphs showing the ELISA results for a calcium phosphate—herpes simplex 2 antigen conjugate according to one embodiment of the present invention. FIG. 9A shows ELISA results with an IgG antibody titer. FIG. 9B shows ELISA results with an IgG2a antibody titer. FIG. 9C shows ELISA results with an IgG1 antibody titer. FIG. 9D shows ELISA results with an IgE antibody titer.

FIG. 10 presents a series of graphs showing the ELISA results for a calcium phosphate—tuberculosis antigen conjugate according to one embodiment of the present invention. FIG. 10A shows ELISA results with an IgG antibody titer. FIG. 10B shows ELISA results with an IgG2a antibody titer. FIG. 10C shows ELISA results with an IgG1 antibody titer. FIG. 10D shows ELISA results with an IgE antibody titer.

FIG. 11 presents a series of graphs showing the ELISA results for a calcium phosphate—ovalbumin antigen conjugate according to one embodiment of the present invention. FIG. 11A shows ELISA results with an IgG antibody titer. FIG. 11B shows ELISA results with an IgG2a antibody titer. FIG. 11C shows ELISA results with an IgG1 antibody titer. FIG. 11D shows ELISA results with an IgE antibody titer.

FIG. 12 is a schematic drawing showing a calcium phosphate core particle (4) both coated with antigenic material or natural immunoenhancing factor (8) and having antigenic material or natural immunoenhancing factor (8) impregnated therein.

FIG. 13 is a series of schematic drawings showing embodiments having a calcium phosphate core particle (4) coated with material (6), such as antigenic material, natural immunoenhancing factors, polynucleotide material encoding immunogenic polypeptides, or therapeutic proteins or peptides, or having material (6) impregnated therein. FIG. 13A shows a core particle coated directly with material (6). FIG. 13B shows a core particle (4) coated with surface modifying agent (2), such as polyethylene glycol or cellobiose, and a having a material (6) adhered to the surface modifying agent (2). FIG. 13C shows a calcium phosphate core particle (4) having a surface modifying agent (2), such as polyethylene glycol or cellobiose incorporated therein and having a material (6) at least partially coating core particle (4).

FIG. 14 is a schematic drawing showing a calcium phosphate core particle (4) having both a surface modifying agent (2), such as polyethylene glycol or cellobiose and a material (6), such as antigenic material, natural immunoenhancing factors, polynucleotide material encoding immunogenic polypeptides, or therapeutic proteins or peptides incorporated therein.

FIG. 15 is a graph showing blood glucose levels over time before and after administration of a calcium phosphate core particle having insulin coated on the surface.

DETAILED DESCRIPTION OF SPECIFIC EMBODIMENTS OF THE INVENTION

The present invention relates to novel calcium phosphate core particles, to methods of making them, and to methods of using the core particles as vaccine adjuvants, as cores or carriers for biologically active material, and as controlled release matrices for biologically active material. The present invention also relates to the novel calcium phosphate core particles having a material at least partially coated on the surface of the core particles, or dispersed or impregnated within the core particles, to methods of making them, and to methods of using them. Non-limiting examples of a suitable material to be at least partially coated on the surface of the core particle or impregnated therein include antigenic material, natural immunoenhancing factor(s), polynucleotide material encoding immunogenic polypeptides, or therapeutic proteins or peptides.

The core particles of the present invention may optionally have at least a partial coating of a surface modifying agent, which may help adhere the above-mentioned material to the core particle, or may have a surface modifying agent impregnating the particle, or both.

One embodiment of the present invention relates to calcium phosphate core particles suitable for adjuvanting vaccines, the particles being administerable in their uncoated state. The core particles are also suitable for use as supports for microbial antigenic material or natural immunoenhancing factor (as cores to be at least partially coated with microbial antigenic material or natural immunoenhancing factor) and for providing a controlled or sustained release matrix for biologically active molecules. As used herein, the term "antigenic material" or "antigen" means an immunogenic antigen product obtained from a bacteria, virus, or fungus, and containing one or more antigenic determinants. Examples of antigenic material as this term is used herein include one or more portions of the protein coat, protein core, or functional proteins and peptides of a virus, such as Epstein-Barr virus (EBV), human immunodeficiency virus (HIV), human papilloma virus (HPV), herpes simplex virus (HSV), pox virus, influenza, or other virii, or immunogenic proteins obtained from bacteria, such as tuberculosis (TB), staphylococcal, streptococcal, clostridium, pseudomonas, or coliform bacterial antigens, or fungi, such as candida and other saccharomyces. The binding activity of calcium phosphate core particles allows a high loading capacity for these different types of proteins.

The particles of the present invention can also be coated (with or without an intermediate coating of a surface modifying agent) or impregnated with natural immunoenhancing factors. These are typically proteins or peptides that function as natural adjuvants, stimulating the response of the immune system to antigenic challenge by a vaccine antigen. Suitable natural immunoenhancing factors include interleukins, including those already recognized to have immunoenhancing activity, such as interleukin-2 and interleukin-12, and those discovered in the future to have such activity.

Another embodiment of the present invention relates to calcium phosphate core particles modified to function as polynucleotide vaccines, having DNA or RNA encoding immunogenic polypeptides at least partially coated on the surface of the core particles or at least partially impregnated therein. Exemplary polynucleotides include those encoding immunogenic epitopes for influenza, malaria, colon cancer cells, hepatitis B, human immunodeficiency virus (HIV), simian immunodeficiency virus (SIV), cutaneous T cell lymphoma, herpes simplex, tick born encephalitis, rabies, rotavirus, tuberculosis, Epstein-Barr virus, human papilloma virus, and hepatomavirus. When administered to a patient, the core particle biodegrades and the DNA or RNA is taken up and expressed by the cells and translated to produce one or more immunogenic polypeptides that are recognized by the immune system.

Another embodiment of the present invention relates to calcium phosphate core particles that deliver therapeutic proteins or peptides, and in particular, a hormone, such as insulin, to a patient in need thereof The core particles are administerable via inhalation.

I. Core Particles

The calcium phosphate core particles of the present invention have an average particle size between about 300 nm and about 4000 nm, more particularly, between about 300 nm and about 2000 nm. For the applications described herein, an average particle size of between about 300 nm and 1000 nm is sufficient and desirable. The core particles of the present invention have a morphology that is generally and substantially spherical in shape and a surface that is substantially smooth.

The term "substantially smooth" is used herein to mean essentially no surface features or irregularities having a size of 100 nm or larger. The core particles may be faceted or angular and still fall within this definition, as long as the facets do not contain many surface irregularities of the type described above. The term "substantially spherical" is used herein to refer to particles that are substantially round or oval in shape, and includes particles that are unfaceted and smooth, or that have very few facets, as well as particles that are polyhedral having several or numerous facets. Substantially smooth, substantially spherical particles according to the invention are visible in scanning electron micrographs and shown in FIGS. 1A and 1B.

The following table provides a comparison between the calcium phosphate core particles of the present invention and calcium phosphate particles manufactured by Superfos Biosector a/s, referred to as "Accurate CAP" in FIGS. 7A–C. The table shows that the calcium phosphate core particles of the present invention are small, smooth and ovoid, whereas Superfos Accurate CAP particles are large, jagged and crystalline.

|  | BioSante Pharmaceuticals, Inc. CAP | Superfos Biosector a/s CAP |
| --- | --- | --- |
| pH | 6.2–6.8 | 6.49 |
| Size | <1000 nm | >3000 nm |
| Morphology | Smooth ovoid shape | Jagged crystalline shape |
| Antibody response: | | |
| IgG | See Figure 7A | See Figure 7A |
| IgG1 | See Figure 7B | See Figure 7B |
| IgG2a | See Figure 7C | See Figure 7C |

The calcium phosphate core particles of the present invention are typically prepared as a suspension in aqueous medium by reacting a soluble calcium salt with a soluble phosphate salt, and more particularly, by reacting calcium chloride with sodium phosphate under aseptic conditions. Initially, an aqueous solution of calcium chloride having a concentration between about 5 mM and about 100 mM is combined by mixing with an aqueous solution of a suitable distilled water-based solution of sodium citrate, having a concentration between about 5 mM and about 100 mM. The presence of sodium citrate contributes to the formation of an electrostatic layer around the core particle, which helps to stabilize the attractive and repulsive forces between the core particles, resulting in physically stable calcium phosphate core particles.

An aqueous solution of dibasic sodium phosphate having a concentration between about 5 mM and about 100 mM is then mixed with the calcium chloride/sodium citrate solution. Turbidity generally forms immediately, indicating the formation of calcium phosphate core particles. Mixing is generally continued for at least about 48 hours, or until a suitable core particle size has been obtained, as determined by sampling the suspension and measuring the core particle size using known methods. The core particles may be optionally stored and allowed to equilibrate for about seven days at room temperature to achieve stability in size and pH prior to further use.

In one embodiment, the calcium phosphate core particles of the present invention can be used without further modification as vaccine adjuvants. For instance, the core particles may be uncoated and can be administered in a dosage of about 1 µg to about 1000 µg per kilogram of total body weight in conjunction with killed, attenuated, or live vaccines, with decoy viruses, or with core particles at least partially coated with microbial antigenic material, such as those described above. The killed, live, or attenuated vaccines, decoy viruses, or antigen-coated core particles may be administered in the same solution as, or in a different solution from, that of the uncoated particles.

In another embodiment, the core particles of the present invention can also be at least partially coated with material, wherein the material is disposed on the surface of the core particle and optionally held in place by a surface modifying agent sufficient to bind the material to the core particle without denaturing the material. Non-limiting examples of the material disposed on the surface of the core particles include antigenic material or natural immunoenhancing factor, polynucleotide material, or therapeutic proteins or peptides.

Surface modifying agents suitable for use in the present invention include substances that provide a threshold surface energy to the core particle sufficient to bind material to the surface of the core particle, without denaturing the material. Example of suitable surface modifying agents include those described in U.S. Pat. Nos. 5,460,830, 5,462,751, 5,460,831, and 5,219,577, the entire contents of each of which are incorporated herein by reference. Non-limiting examples of suitable surface modifying agents may include basic or modified sugars, such as cellobiose, or oligonucleotides, which are all described in U.S. Pat. No. 5,219,577. Suitable surface modifying agents also include carbohydrates, carbohydrate derivatives, and other macromolecules with carbohydrate-like components characterized by the abundance of—OH side groups, as described, for example, in U.S. Pat. No. 5,460,830. Polyethylene glycol (PEG) is a particularly suitable surface modifying agent.

The core particles may be at least partially coated by preparing a stock solution of a surface modifying agent, such as cellobiose or PEG (e.g., around 292 mM) and adding the stock solution to a suspension of calcium phosphate core particles at a ratio of about 1 mL of stock solution to about 20 mL of particle suspension. The mixture can be swirled and allowed to stand overnight to form at least partially coated core particles. The at least partially coated core particles are administerable alone or in conjunction with one or more of the materials described below. Generally, this procedure will result in substantially complete coating of the particles, although some partially coated or uncoated particles may be present.

II. Antigenic Material or Natural Immunoehancing Factor

Figure 12:
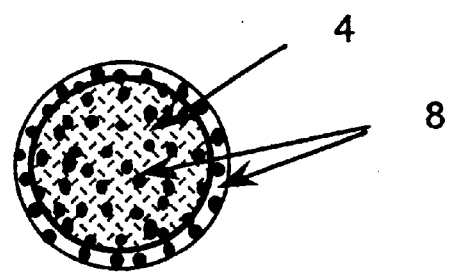

In one embodiment, the uncoated core particles or the core particles at least partially coated with surface modifying agent are then contacted with antigenic material or natural immunoenhancing factor, to produce particles having antigenic material or natural immunoenhancing factor at least partially coating the core particle. FIG. 12 is a schematic drawing of the particles of this embodiment, illustrating antigenic material or natural immunoenhancing factor (8) both coating the core particle (4) and incorporated within the core particle (4) (as will be discussed below). Antigen purified from viral coat or capsule proteins, or from cell surfaces of bacteria or fungi, can be obtained or purified using methods that are known in the art, or can be obtained commercially. For example, viral particles are obtained by infecting transforming host cell lines with the virus, and after a suitable incubation period, centrifuging the cell suspension and sonicating the resulting suspension at high power for several minutes to break open the cells, and again centrifuging the broken cell suspension. The supernatant containing virus can then be stored for further processing and protein purification using techniques familiar to those skilled in the art. Bacterial and fungal cell membrane antigens can be obtained by culturing and lysing the desired organisms and separating the desired antigenic protein fractions using techniques known in the art.

The antigen-coated particles of the invention are not produced by methods requiring the denaturing of the protein coating of a viral particle, removal of the core viral genetic material, and renaturing of the protein coating around a substitute core. Instead, the antigen-coated particles of the invention result from attachment of individual portions of protein coating to a calcium phosphate core. As a result, the particles of the invention are not believed to function as "decoy viruses" per se, as described in several of the patents cited above.

Instead, the particles of the invention can be more potent immunogenically than can a decoy virus, since only immunogenic portions of proteins need be attached to the particles. This increases the likelihood, for a given concentration of particles, that an antigenic epitope on the particle will elicit an immune response. In addition, the particles of the invention can be used to provide a broader spectrum of protection, since immunogenic material from several different pathogens can be attached to the surface of a single particle, or to the surfaces of different particles administered substantially simultaneously. These advantages are not obtained with the viral decoy particles described in the above-identified patents.

In addition to an antigen coating or in the alternative, the calcium phosphate core particles of the present invention can be prepared as controlled release particles for the sustained release of antigenic material or natural immunoenhancing factor over time, wherein the antigenic material or natural immunoenhancing factor (8) is incorporated into the structure of the core particle (4), shown in FIG. 12. This is done by mixing the aqueous calcium chloride solution with the antigenic material or natural immunoenhancing factor to be incorporated prior to combining and mixing with either the sodium citrate or dibasic sodium phosphate solutions, to co-crystallize the calcium phosphate core particles with the antigenic material or natural immunoenhancing factor. The antigenic material may consist of an immunogenic antigen product obtained from a bacteria, virus, or fungus, and containing one or more antigenic determinants, as described in detail above. The natural immunoenhancing factor may consist of proteins or peptides that function as a natural adjuvant, such as interleukins, particularly interleukin-2 and interleukin-12, also described in detail above.

III. Polynucleotide Material

If polynucleotide material is coated onto and/or incorporated within the core particle, the particles function as a controlled release matrix for the DNA or RNA. The DNA or RNA that is at least partially coated onto or incorporated within the core particles may be selected from a wide variety of DNA or RNA sequences that encode epitopes of one or more immunogenic polypeptides, and thus can be used as the active ingredient in a DNA or RNA vaccine. Antisense fragments may also be used. Exemplary polynucleotides include those encoding immunogenic epitopes for influenza, malaria, colon cancer cells, hepatitis B, human immunodeficiency virus (HIV), simian immunodeficiency virus (SIV), cutaneous T cell lymphoma, herpes simplex, tick born encephalitis, rabies, rotavirus, tuberculosis, Epstein-Barr virus, human papilloma virus, and hepatomavirus.

The polynucleotide can be naked or inserted into a plasmid vector. Suitable plasmids are known to those skilled in the art, and typically include pcDNA3 (Invitrogen), pCI (Promega) and PBR231. It may be desirable that the plasmid or naked DNA express cytomegalovirus (CMV) intermediate-early promoter, or bovine growth hormone polyadenylation sequence. A large number of expression vectors can be constructed by incorporating a cDNA sequence encoding an immunogenic polypeptide into a plasmid vector. The DNA or RNA segments may be prepared, inserted into vectors, and the vectors cloned according to known procedures, such as the procedures described in Maniatis, et al., *Molecular Cloning*, Cold Spring Harbor Laboratory Press, New York, 1.0–19.0 (1989). Gene segments are also available commercially from a number of different suppliers, and inserted into commercially available plasmids. When the sequence of a candidate protein is known, a coding sequence of the polynucleotide can typically be inferred and the corresponding gene segment prepared and isolated.

The polynucleotide sequence may be fused with other sequences in the vector, such as human tissue plasminogen activator leader peptide. The vectors can also include bacterial DNA or naked DNA surrounding the gene for the pathogenic antigen as a foreign sequence motif, increasing the immune response to that gene. See Y. Sato et al., *Science* 273:352–354 (1996); G. J. Weiner et al., *PNAS* 94(20): 10833–7 (1997). Moreover, the plasmid may also include other genetic adjuvants, such as genes coding for cytokines, such as granulocyte-macrophage colony-stimulating factor (GM-CSF) or interleukins, to further multiply the immune response.

Figure 13A:
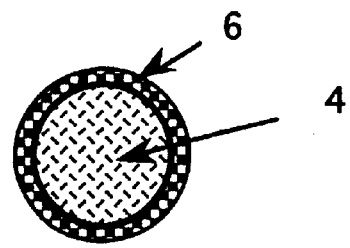
Figure 13B:
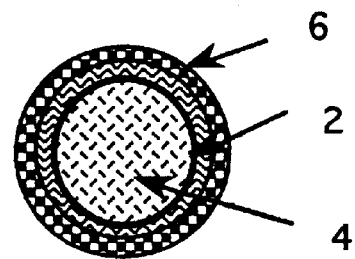

To form core particles having at least a partial coating of polynucleotide material, the at least partially coated core particles described above are contacted with polynucleotide material, i.e., DNA or RNA coding for one or more antigens expressed by organisms to be vaccinated against. When the core particles are coated, the DNA or RNA material is attached to the surface of the coating as described in U.S. Pat. No. 5,460,831. FIG. 13A shows a schematic drawing of the particles of this embodiment, with material (6), such as polynucelotide material coating the core particle (4).

In addition to a polynucleotide coating or in the alternative, polynucleotide material may be incorporated into the structure of the core particle. For example, the DNA or RNA coding for an epitope expressed on a viral protein coat or capsule can be mixed with a solution of calcium chloride, which can then be mixed with, e.g., a buffer, such as a sodium citrate solution, and a solution of dibasic sodium phosphate. The resulting particles will have the DNA or RNA dispersed or impregnated therein. A vector containing the DNA or RNA may also be added with one or more of the reactants forming the core particle, as described above. For example, a plasmid or other vector containing immunogen-encoding DNA or RNA or naked DNA can be mixed with the calcium chloride solution, so that the calcium phosphate biodegradable matrix forms around the plasmid or naked DNA, which becomes embedded in and/or on the core particle.

The impregnated or coated core particle fragments can be separated from the production mixture and stored for further use. Storage can be by any conventional methods for storing gene segments or antisense fragments. For example, the core particles may be lyophilized or stored as a suspension in a compatible solution.

A typical polynucleotide vaccine produced according to the present invention contains about 0.5 to 500 micrograms of DNA or RNA material. When administered, the core particles are combined with a pharmaceutically acceptable carrier solution or other excipient. The dose will vary with the route of administration, the frequency of treatment, and other patient characteristics. Typical vaccination dosages include from about 0.1 mL to 2 mL of a vaccine containing about 0.5 to 500 micrograms of DNA or RNA material. Because the core particle supporting the DNA or RNA is biodegradable calcium phosphate, DNA or RNA that may impregnated therein is slowly released over time as the particles dissolve under physiological conditions. DNA or RNA released from the dissolving material is taken up and expressed by cells, and translated to produce one or more immunogenic polypeptides that are recognized by the humoral and cell-mediated immune system in the same manner as if the antigen had been vaccinated conventionally, but without the risks associated with the administration of live attenuated or killed virus. Moreover, the presence of calcium phosphate particles that have not completely dissolved serves an adjuvanting function for the DNA or RNA vaccine by enhancing the efficacy of the immunogenic protein or proteins expressed by the cells taking up the DNA or RNA.

IV. Therapeutic Protein or Peptide

In still a further embodiment, the at least partially coated core particles described above support a therapeutically effective protein or peptide. In addition, or in the alternative, the calcium phosphate core particles of the present invention can be prepared as controlled release particles for the sustained release of the therapeutic protein or peptide over time, wherein the therapeutic protein or peptide is incorporated into the structure of the core particle.

The core particles that are at least partially coated and/or impregnated with a therapeutic protein or peptide may function as an inhalable aerosol. This protein or peptide may be any therapeutically effective protein or peptide, and in particular may be a hormone, such as insulin, especially human insulin. Core particles coated or impregnated with a material (6), such as a therapeutic protein or peptide, and more particularly human insulin, are shown in FIGS. 13 and 14.

Coating of the core particles with a therapeutic protein or peptide is preferably carried out by suspending the core particles in a solution containing a dispersed surface modifying agent, generally a solution of double distilled water containing from about 0.1 to about 30 wt % of the surface modifying agent. The cores are maintained in the surface modifying agent solution for a suitable period of time, generally about one hour, and may be agitated, e.g., by rocking or sonication. The at least partially coated core particles can be separated from the suspension, including from any unbound surface modifying agent, by centrifugation. The at least partially coated core particles can then be resuspended in a solution containing the protein or peptide to be adhered to the at least partially coated core particle.

Optionally, a second layer of surface modifying agent may also be applied to the protein or peptide adhered to the particle.

In another embodiment, a protein or peptide may be attached to an unmodified particle surface, although particles at least partially coated with a surface modifying agent have greater loading capacities. For example, insulin loading capacities of at least partially coated particles have been found to be about 3 to 4-fold higher than insulin loading capacities of unmodified particle surfaces. Additionally, an increase in particle size may result in a greater loading capacity. For instance, an increase of 150 nm in particle size (relative to a starting size of 450 nm to 600 nm) results in about a 3-fold increase in insulin loading capacity in particles that are at least partially coated with a surface modifying agent.

Figure 13C:
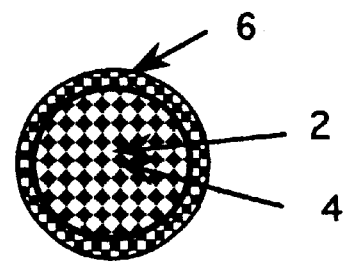

Another embodiment that facilitates higher loading capacities is schematically illustrated in FIG. 13C, which shows a core particle having a surface modifying agent (2), such as polyethylene glycol, impregnated therein. The particles may be prepared by adding a surface modifying agent (2) to one or more of the aqueous solutions forming the core particle (4). The core particles may optionally be stored at room temperature. To obtain at least partially coated particles, the particles are subsequently contacted with a therapeutic protein or peptide, such as insulin, and more particularly human insulin, to provide at least a partial coating on the particle as described above.

Figure 14:
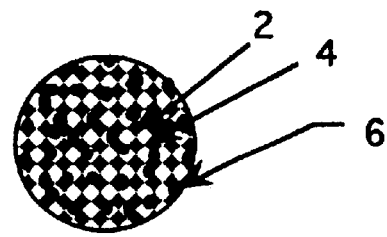

A further embodiment facilitating higher loading capacities is illustrated in FIG. 14, which shows a core particle (4) having both a surface modifying agent (2), such as polyethylene glycol, and a material (6), such as therapeutic protein or peptide, more particularly insulin, and even more particularly human insulin, impregnated therein. One way in which particles of this embodiment may be prepared is by combining human insulin and/or other desired protein or peptide and a surface modifying agent together to form a solution. This solution is then combined with one or more of the aqueous solutions forming the particle as described above. The resulting particles incorporate calcium phosphate, surface modifying agent, and insulin within the core particle. Particles prepared according to this and any other embodiments described herein may be combined with one or more particles prepared according to any other embodiment described herein.

In a more particular embodiment, the composition of the present invention comprising a calcium phosphate core at least partially coated with polyethylene glycol and human insulin may be administered to diabetic patients as an aerosol of the dried particles, or as an aerosol of a solution of the particles in a carrier liquid, such as water. The particular insulin dose delivered corresponds to that given intravenously and by other methods, and the dose of particulate insulin given is determined based on the blood glucose levels and supplied dosages of particles in the rat model described herein. Without wishing to be bound to the following dosage ranges, average daily doses of about 0.5 to about 2.0 mg are believed to be appropriate to generate a therapeutic effect in humans.

Incorporating a therapeutic protein or peptide into the particle may be accomplished by mixing an aqueous calcium chloride solution with the therapeutic protein or peptide to be incorporated prior to combining and mixing with either the sodium citrate or dibasic sodium phosphate solutions, to co-crystallize the calcium phosphate core particles with the therapeutic protein or peptide.

The particles, vaccines, and pharmaceutical compositions of this invention may be suitably administered to any patient in need thereof, namely to any species of animal that suffers or can suffer from the disease conditions described herein, more particularly mammals, and even more particularly humans.

The various embodiments of the invention can be more clearly understood by reference to the following nonlimiting examples.

EXAMPLE 1

A 12.5 mM solution of $CaCl_2$ is prepared by mixing 1.8378 g of $CaCl_2$ into 800 mL of sterile GDP water under aseptic conditions until completely dissolved, and the solution diluted to 1 L and filtered. A 15.625 mM solution of sodium citrate was prepared by dissolving 0.919 g of sodium citrate into 200 mL of sterile GDP water with mixing using aseptic techniques and filtered. A 12.5 mM solution of dibasic sodium phosphate was prepared by dissolving 1.775 g sodium phosphate into 1 L of sterile GDP water with mixing using aseptic techniques and filtered. All solutions were stored at room temperature.

Figure 1B:
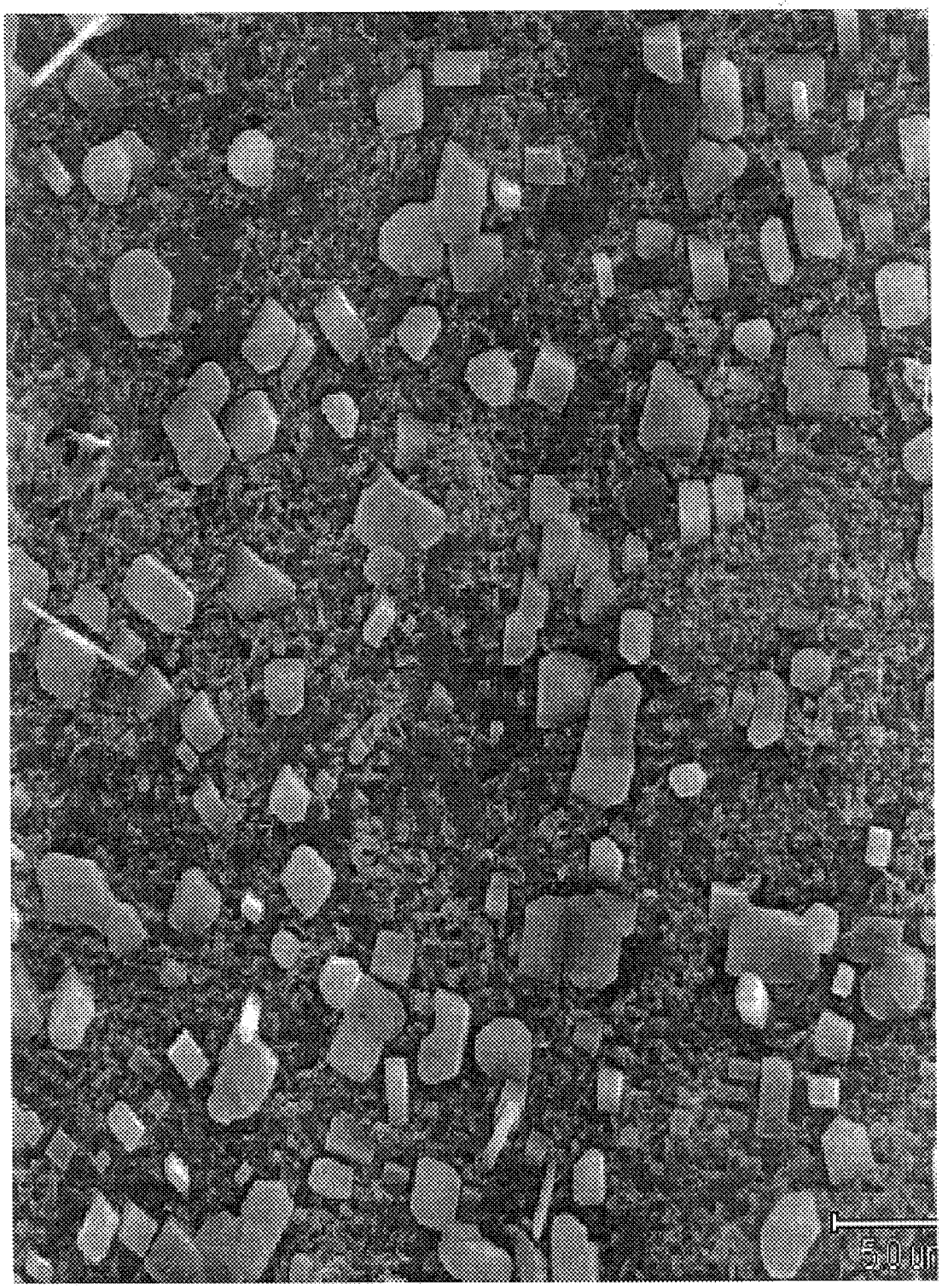

The calcium chloride solution was combined with the sodium citrate solution and thoroughly mixed. Subsequently, the sodium phosphate solution was added with mixing. Turbidity appeared immediately as particles began to form. The suspension was allowed to mix for several minutes and was sampled for endotoxin testing using aseptic technique. Mixing was continued for about 48 hours under a laminar flow hood. Following mixing, the particles were sonicated on a high power setting for about 30 minutes at room temperature, tested for endotoxin concentration and pH and characterized as to particle size with a Coulter N4Plus Submicron Particle Sizer. Photomicrographs of particles prepared in this way are shown in FIGS. 1A and 1B. Following preparation the particles were allowed to equilibrate for approximately seven days before use.

EXAMPLE 2

An HSV-2 protein solution and an Epstein-Barr virus (EBV) protein solution were purified from ATCC VR-540 (infected tissue culture fluid and cell lysate). The viral suspension was contacted with a lysis buffer (1% IGEPAL CA-630 for HSV-2 and 1% Tritonx100 for EBV, 10 mM NaCl, 10 mM Tris-HCL, and 1.5 mM $MgCl_2$), vortexed for 1 minute, incubated on ice for 30 minutes, and centrifuged at 1400 rpm for 2 hours at 4° C. The resulting supernatant was then contacted with a second lysis buffer (1 mM PMSF, 1% IGEPAL CA-630 for HSV-2 and 1% Tritonx100 for EBV, 100 mM NaCl, 100 mM Tris-HCL, and 3 mM $MgCl_2$), incubated on ice for 30 minutes, and centrifuged at 1400 rpm for 2 hours. The supernatant was then dialyzed against 2 L of 0.9% saline overnight, lyophilized and resuspended in 1 mL PBS.

EXAMPLE 3

25 mL of 12.5 mM calcium chloride, 5 mL of 15.625 mM sodium citrate, and 25 mL of 12.5 mM dibasic sodium phosphate solutions were prepared as described in Example 1. The calcium chloride solution was mixed with 1.3 mL of purified HSV-2 protein prepared according to Example 2, which mixing was continued for about 1 minute. 5 mL of sodium citrate was added to the calcium chloride/HSV-2 mixture and allowed to mix for 1 minute. 25 mL of dibasic sodium phosphate was added to the mixture, which immediately becomes turbid, indicating the formation of particles. The mixture is stirred at a moderate speed for 48 to 96 hours, or until the particle size is less than 1000 nm, as determined using a Coulter N4Plus Submicron Particle Sizer, and sonicated. After preparation the particles were stored for approximately seven days before use to allow equilibration of particles to reach size stability.

The resulting particles, containing HSV-2 protein dispersed therein, can be administered as a sustained release vaccine in dosages of about 1 µg to about 250 µg per kg of body weight.

EXAMPLE 4

A suspension of calcium phosphate particles is prepared following the procedures of Example 1, and the particle size and presence of any endotoxin determined. Cellobiose glue is applied to the particles by suspending them in a solution of 292 mM cellobiose stock added to the suspension of calcium phosphate particles at a ratio of 1 mL of cellobiose solution to 20 mL of particle suspension. The mixture is gently mixed and allowed to stand overnight. The at least partially coated particles are then contacted with a solution of cell surface proteins of tuberculosis bacilli (provided by the Morehouse School of Medicine), and co-incubated at room temperature or at 4° C. (as desired).

The resulting particles were characterized by measuring their particle size using a Coulter N4Plus Submicron Particle Sizer, and had an average diameter of <1000 nm.

The efficacy of the particles was tested as follows. Six mice each (for a total of 30 mice) were injected with solutions containing antigen only, calcium phosphate particles only, antigen+Imject (an alum based adjuvant), washed (with PBS three times, with each washing followed by centrifugation at 4500 rpm for 15 minutes at 4° C.) calcium phosphate+antigen, and unwashed calcium phosphate+antigen. The total injection volume for each immunization per mouse was 100 µL.

For the injection of antigen only, the first immunization contained 10 µg of antigen administered intraperitoneally (i.p.), and the second injection contained 10 µg of antigen ("TB only").

For the injection of calcium phosphate particles only, 0.46 mg of this concentrated solution of particles were administered per mouse ("CAP only").

For the injection of antigen+Imject, 10 µg of antigen and 50 mg of alum-based Imject were administered per mouse, i.p. ("TB+Imject").

For the washed calcium phosphate particles+antigen, 10 µg of antigen was coated onto 1.0 mg of calcium phosphate particles, and after washing with PBS, centrifugation, precipitation, and resuspension (three times) was injected i.p. ("Washed CAP-TB").

For the unwashed calcium phosphate particles+antigen, 10 µg of antigen was coated on 1.0 mg calcium phosphate particles and administered i.p., without further treatment ("Unwashed CAP-TB").

Figure 2:
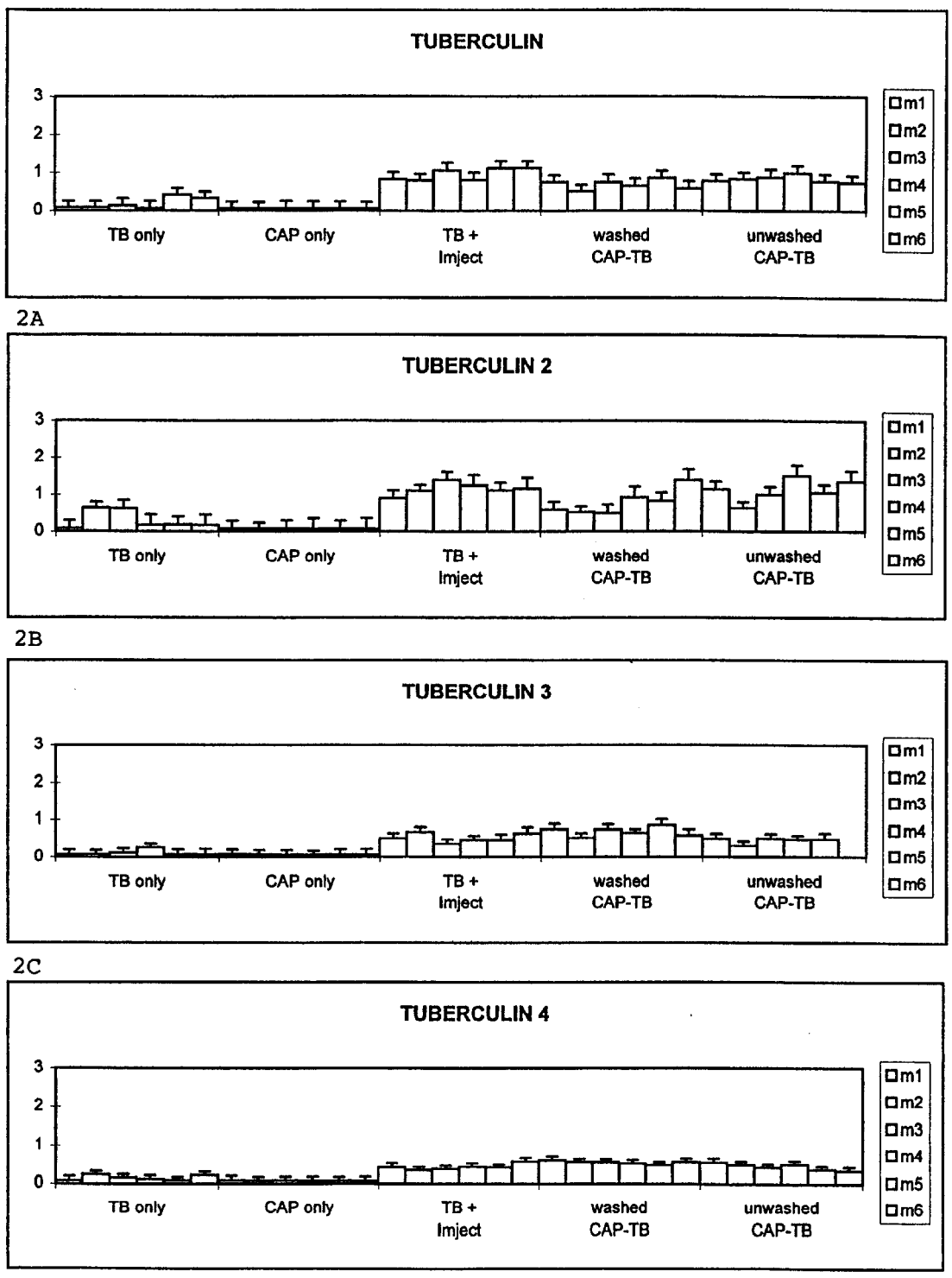
Figure 3:
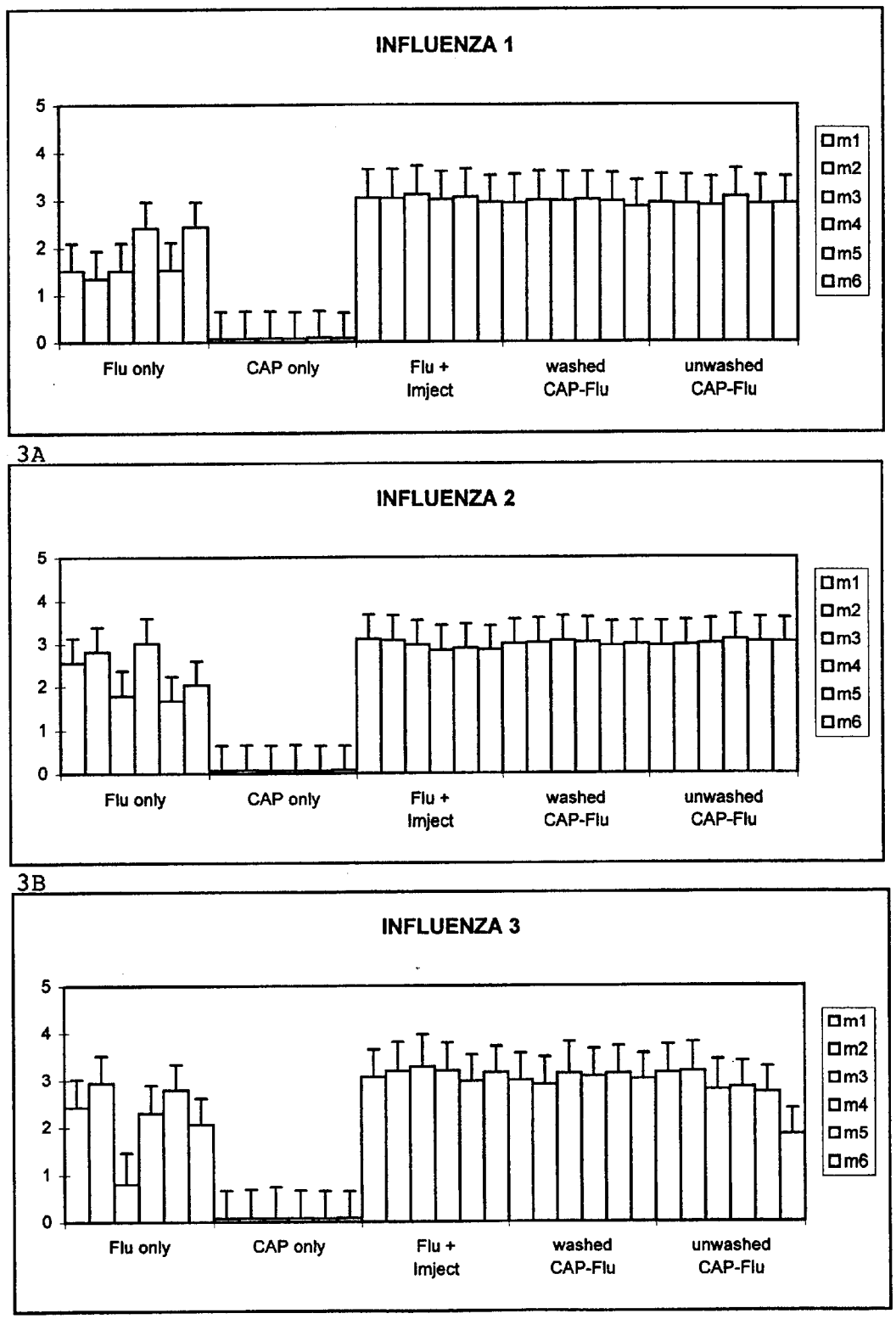

Blood samples were collected approximately three weeks later and subjected to ELISA to measure serum TB-specific antibody. Booster immunizations were given at a concentration of 1 µg approximately 14 days after primary immunization, and blood samples collected and subjected to ELISA about one per month after the booster immunization and about every two months thereafter. The results are provided in FIG. 2.

EXAMPLE 5

25 mL of 12.5 mM calcium chloride, 5 mL of 15.625 mM sodium citrate, and 25 mL of 12.5 mM sodium phosphate dibasic solutions are prepared as described in Example 1. The calcium chloride solution is mixed with of DNA encoding obtained an immunogenic polypeptide of a disease-causing pathogen, prepared according to techniques familiar to those skilled in the art. 5 mL of sodium citrate is added to the calcium chloride/DNA mixture and allowed to mix for 1 minute. 25 mL of dibasic sodium phosphate is added to the mixture, which will immediately become turbid, indicating the formation of particles. The mixture is stirred at a moderate speed for 48 to 96 hours, or until the particle size is less than 1000 nm, as determined using a Coulter N4Plus Submicron Particle Sizer, and sonicated.

The resulting particles, containing DNA encoding an immunogenic polypeptide dispersed therein, can be administered as a sustained release DNA vaccine in dosages of about 1 µg to about 250 µg per kg of body weight.

EXAMPLE 6

Procedures similar to those described above in Examples 4 and 5 were followed, to prepare and evaluate a cellobiose-coated calcium phosphate particle suspension combined with immunogenic herpes simplex 2 viral protein. The protein is prepared from ATTC VR-540 using the protein purification procedures described in Example 2.

50 mL of calcium phosphate suspension prepared as described in Example 1 and coated with cellobiose glue as described in Example 3 were centrifuged at 4500 rpm for 15 minutes at 25° C., and the supernatant discharged. The pellet was resuspended in 2.5 mL of spent buffer from the production of the calcium phosphate particles, so that the calcium phosphate concentration was increased 20 fold. The concentrated calcium phosphate was divided into 1 mL aliquots. 1 mL of HSV protein was added to the concentrated calcium phosphate suspension and rotated for 1 hour at 4° C. One aliquot of this suspension was not washed (UWCCH). The other was washed with PBS (and centrifuged at 4500 rpm for 15 minutes at 4° C.) three times and resuspended in 2 mL PBS (WCCH solution).

50 mL of calcium phosphate co-crystallized with HSV-2 suspension as described in Example 2 were centrifuged at 4500 rpm for 15 minutes at 25° C., and the pellet resuspended in 2.5 mL of spent calcium phosphate buffer. 1 mL of this concentrated calcium phosphate-HSV-2 particle solution was mixed with 1 mL of HSV-2 protein and rotated for 1 hour at 4° C. This solution was washed with PBS (and centrifuged at 4500 rpm for 15 minutes at 4° C.) three times and resuspended in 2 mL PBS (WCHCH solution).

1 mL of Imject (alum adjuvant) was mixed with 1 mL of HSV-2 protein solution (IH).

1 mL of HSV-2 protein solution was mixed with 1 mL of PBS (HIV).

Protein assays were conducted on wash supernatants to determine the percent binding of HSV-2 to the calcium phosphate complexes. Binding was generally >20%.

Immunization testing was carried out as described in Example 3 above, except that a primary immunization and two booster immunizations were administered approximately one month and three weeks apart, respectively. All immunizations were administered intraperitoneally. The amounts administered are provided in the Table below.

| | |
|---|---|
| HSV-2 Only Primary Immunization (HSV) | 52.5 µg antigen |
| HSV-2 Only Second Immunization (HSV) | 89 µg antigen |
| HSV-2 Only Third Immunization (HSV) | 129 µg antigen |
| HSV-2 + Imject (IH) | 52.5 µg HSV-2 antigen 50 mg Imject |
| Washed Calcium Phosphate + HSV-2 (WCCH) | 42.9 µg HSV-2 antigen 0.46 mg Calcium Phosphate |
| Unwashed Calcium Phosphate + HSV-2 (UWCCH) | 52.5 µg HSV-2 antigen 0.46 mg Calcium Phosphate |
| Washed Calcium Phosphate Co-crystallized with HSV-2 + HSV-2 (WCHCH) | 29.1 µg HSV-2 |

Figure 4:
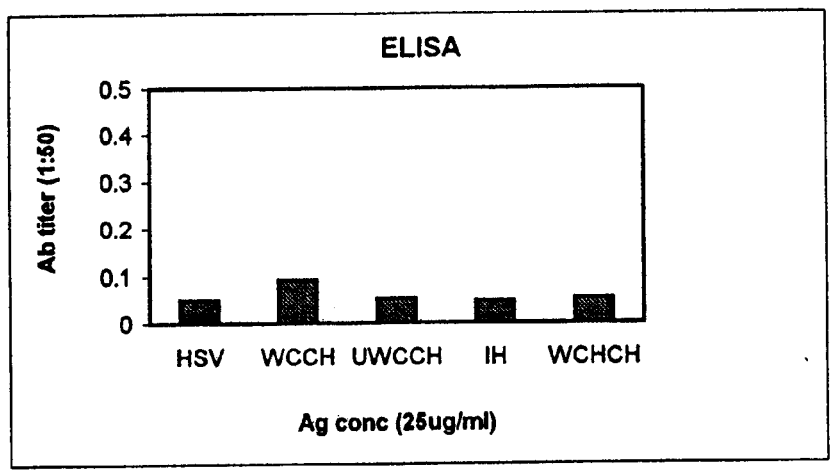
Figure 4:
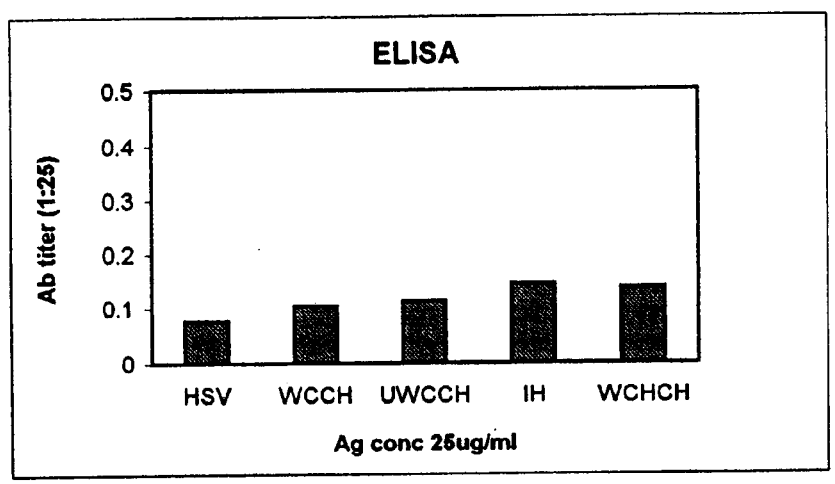
Figure 4:
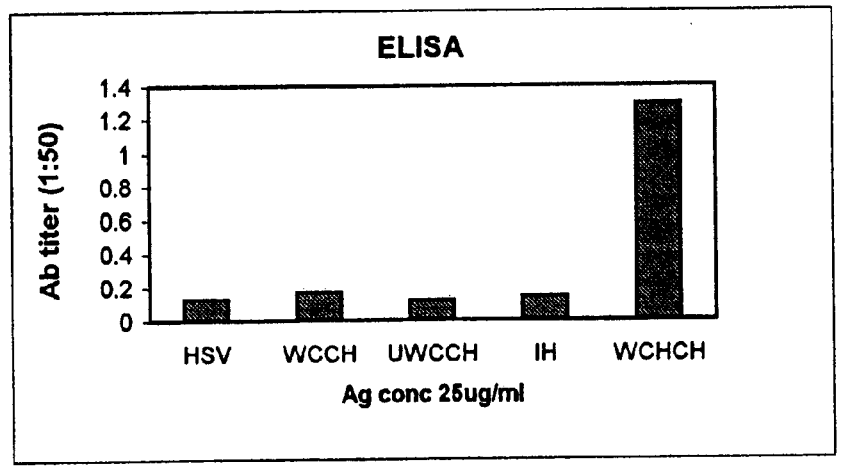
Figure 5:
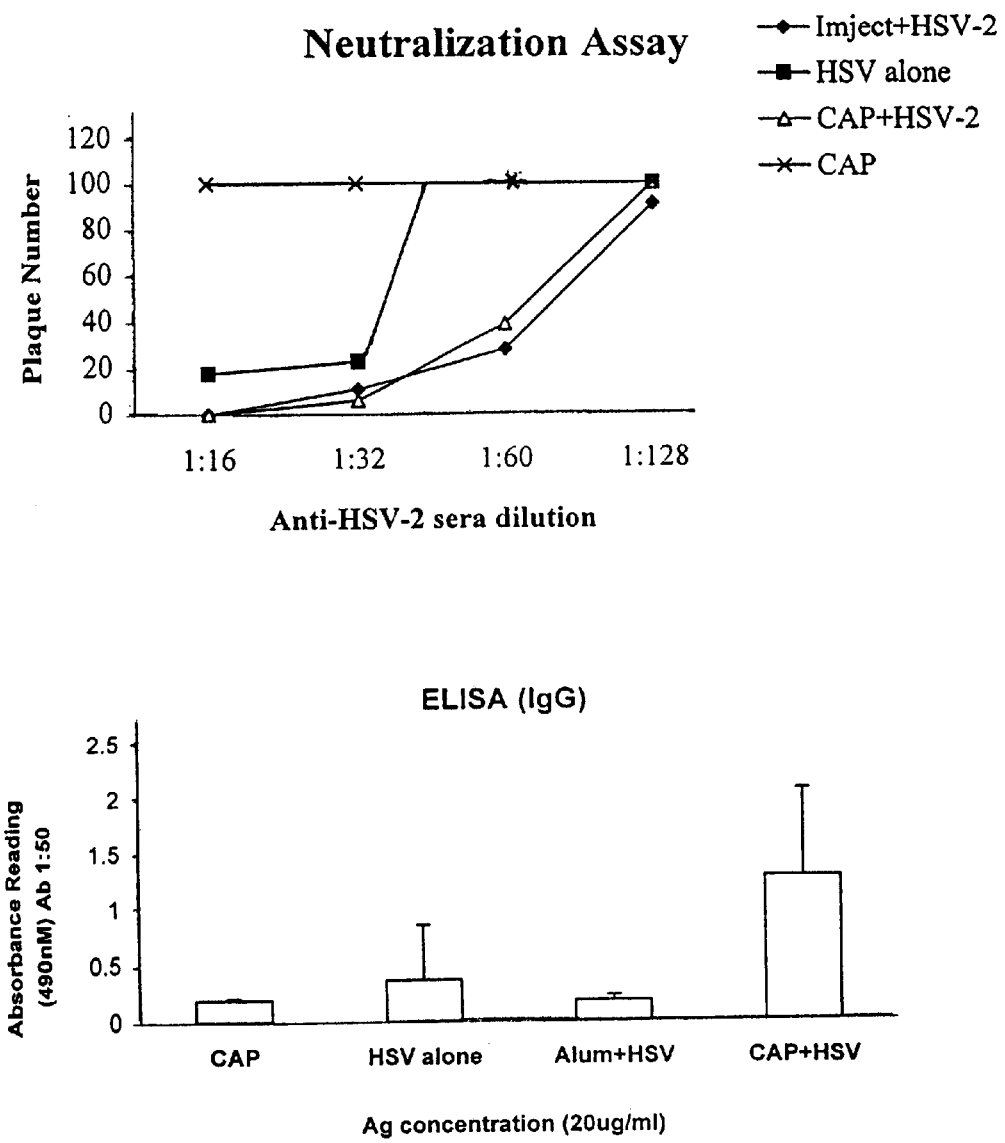

Blood was collected and analyzed by ELISA about one month after the primary injection and about 14 days after each booster injection and again two months after the third ELISA. The results are presented in FIGS. 4 and 5.

Immunized mice were challenged intravaginally with $10^2$ PFU of HSV-2 at 30 days after primary immunization in accordance with the methods discussed in Dr. Rouse et al., 1997, to test resistance. Since the stage of estrus can affect susceptibility to HSV infection, mice were given progesterone injection to synchronize the estrus cycle prior to challenge with HSV-2. The results are presented below.

| | No. of mice survived/ No. of mice challenged | Clinic severity at week Post challenge | | |
|---|---|---|---|---|
| | | 1 | 2 | 3 |
| Control | 3/5 | 1 | 1.3 | 2 |
| Alum + HSV-2 | 5/5 | 0 | 0 | 0 |
| CAP + HSV-2 | 5/5 | 0 | 0 | 0 |

Note:
The mice were observed everyday for vaginal inflammation. Clinic severity was graded as follows: 0. No inflamation; 1. Mild inflamation; 2. Moderate swelling and redness; 3. Severe inflamation; 4. Paralysis; and 5. Death.

EXAMPLE 7

Figure 6:
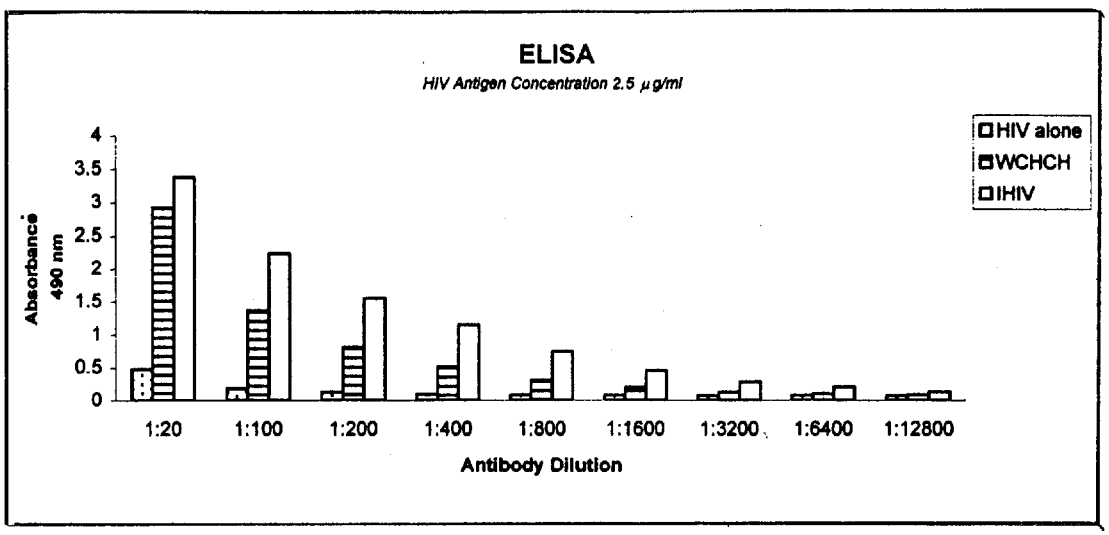
Figure 6:
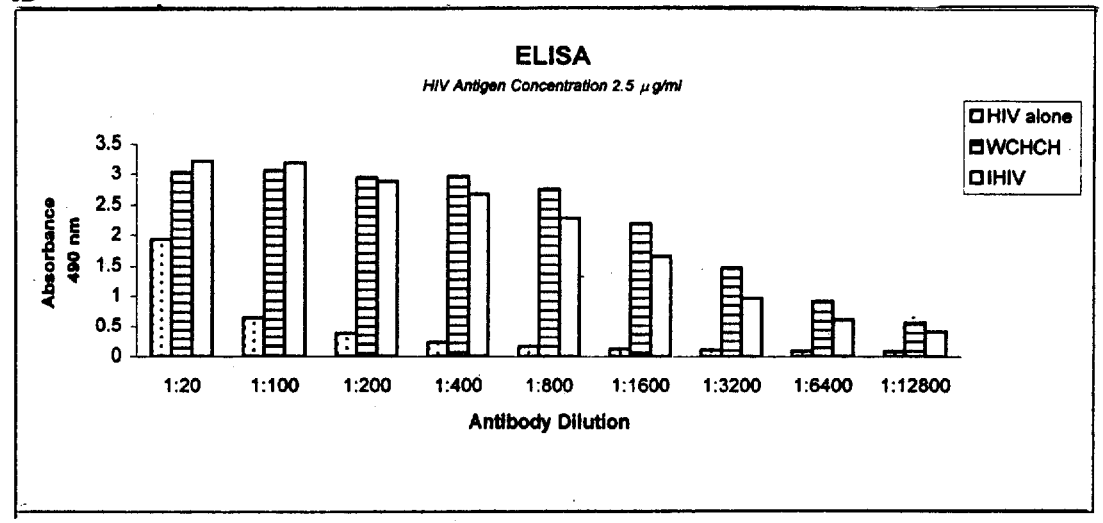
Figure 8:
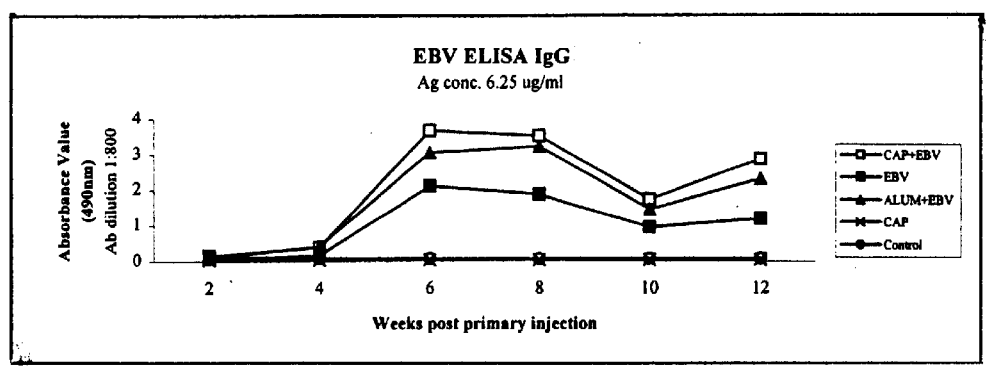
Figure 8:
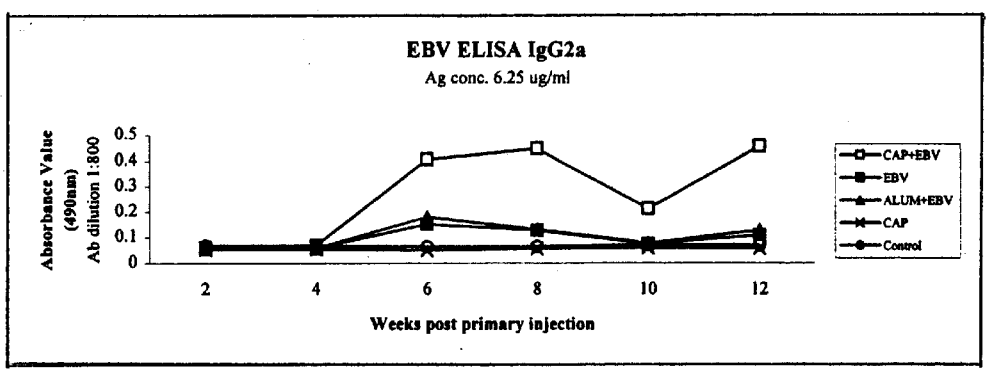
Figure 8:
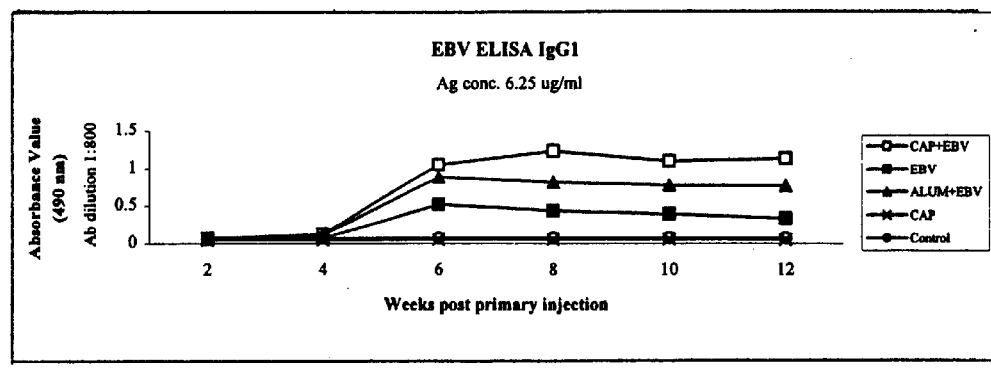
Figure 8:
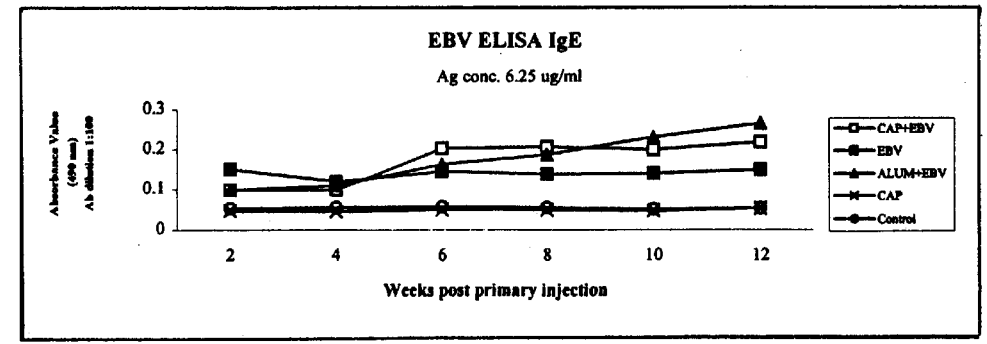
Figure 9:
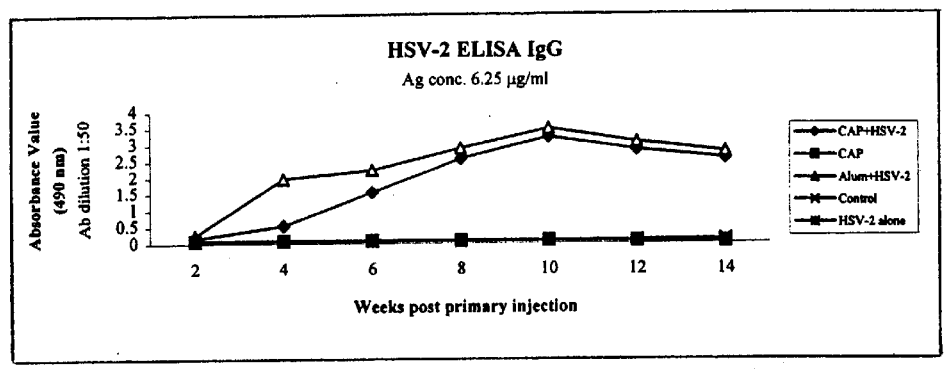
Figure 9:
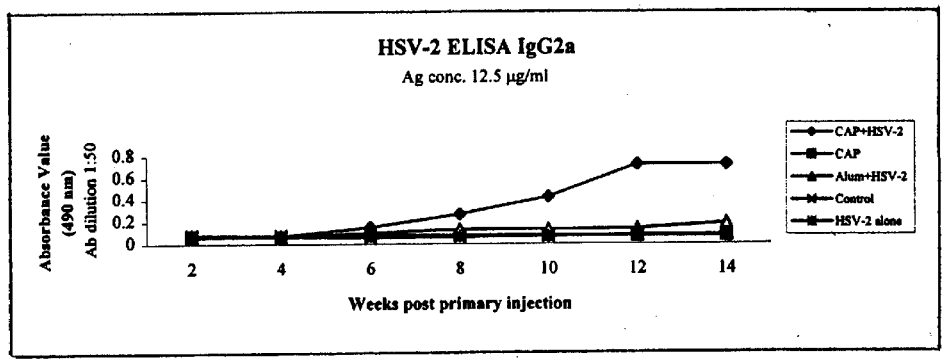
Figure 9:
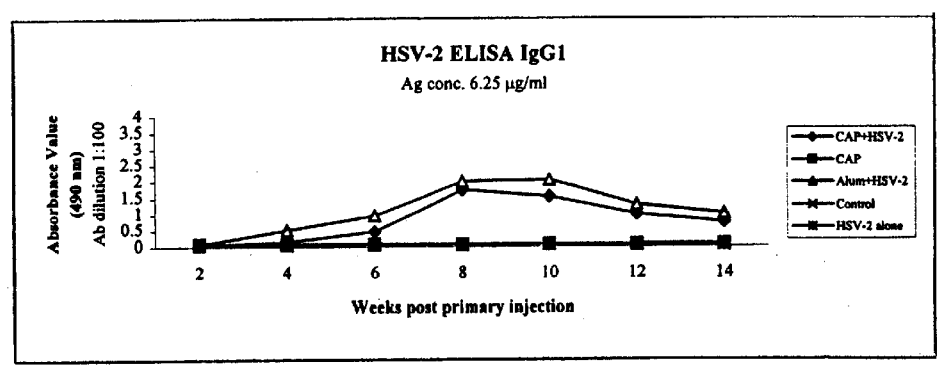
Figure 9:
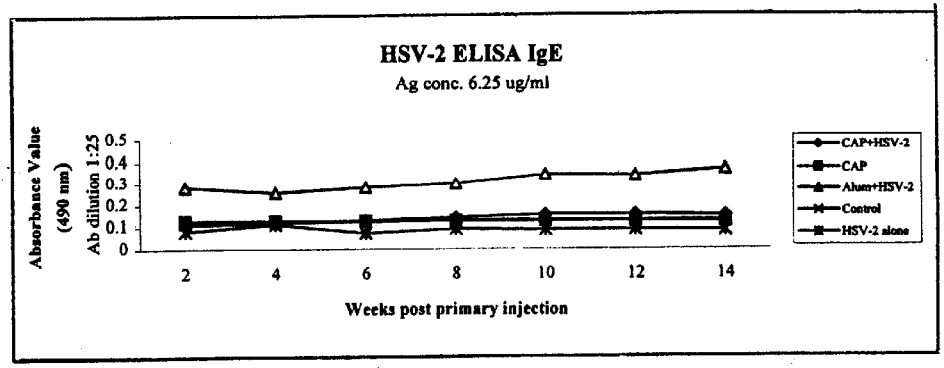
Figure 10:
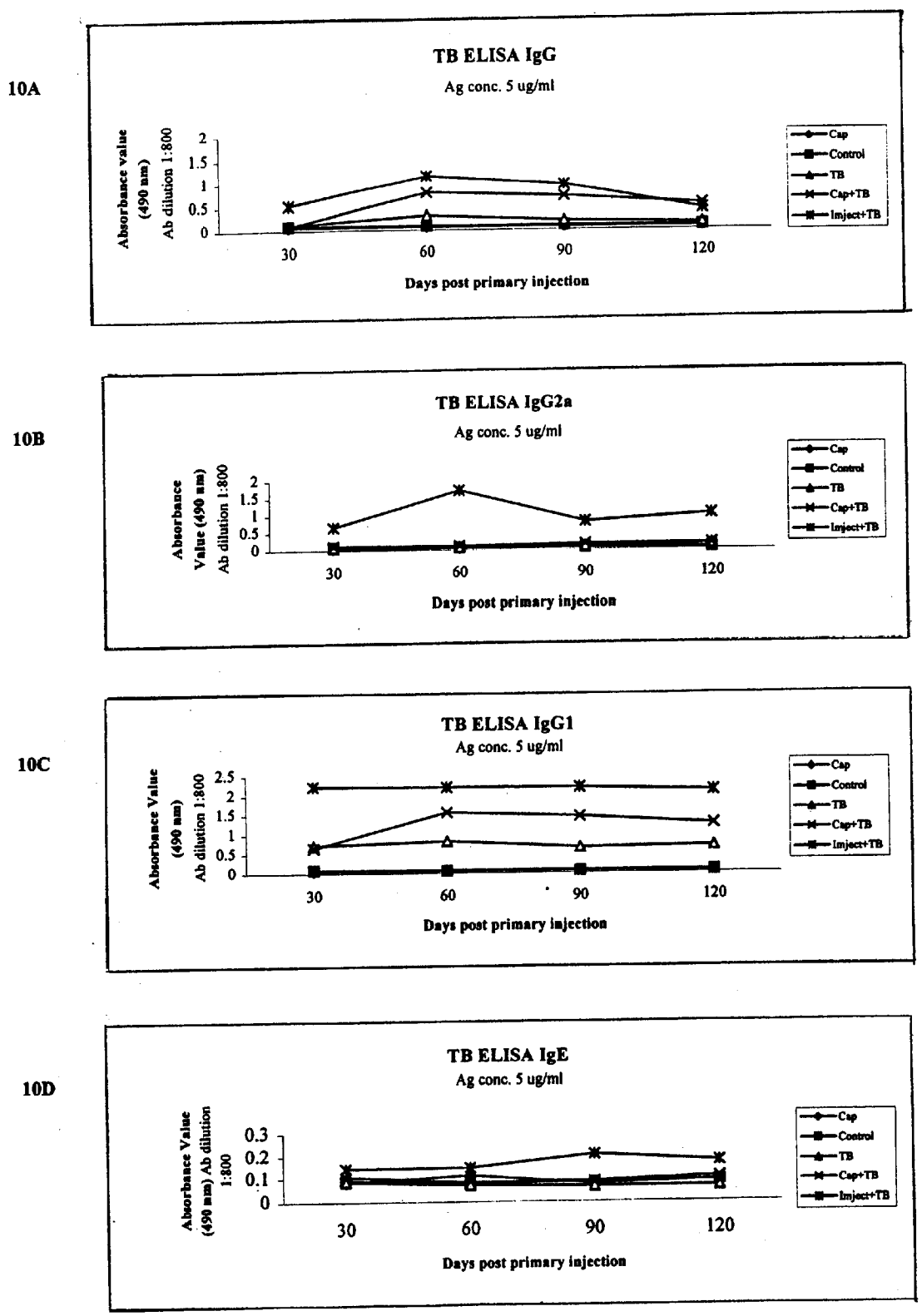
Figure 11:
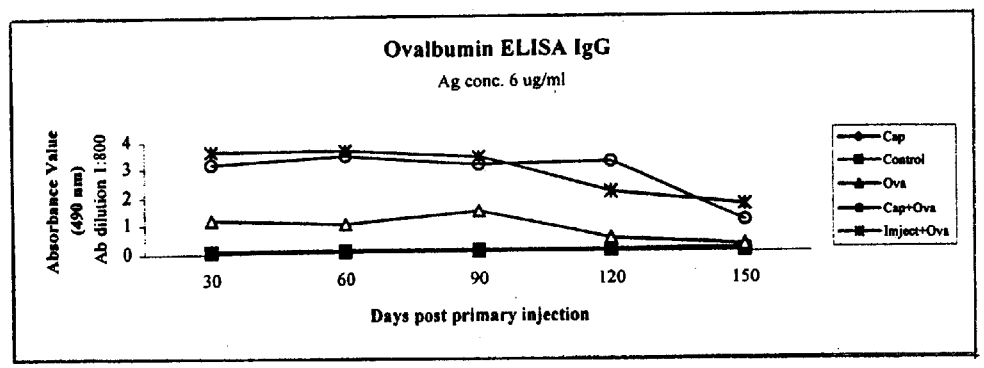
Figure 11:
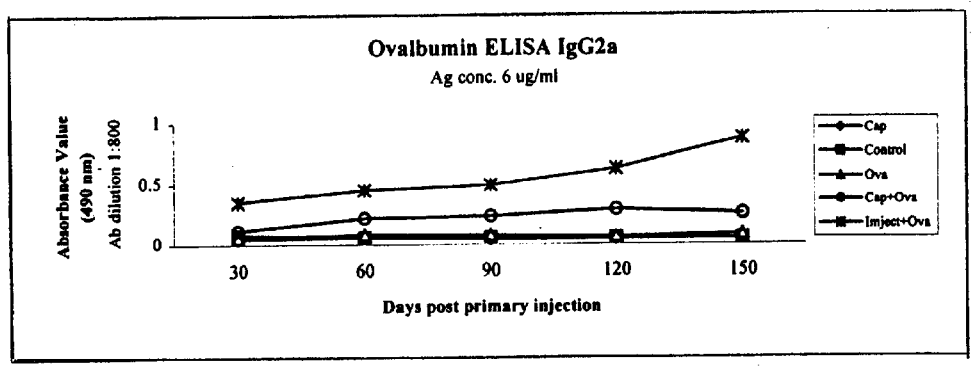
Figure 11:
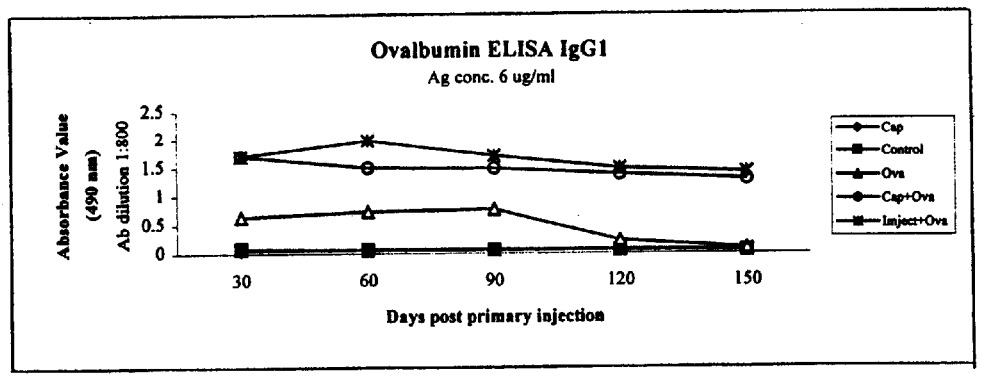
Figure 11:
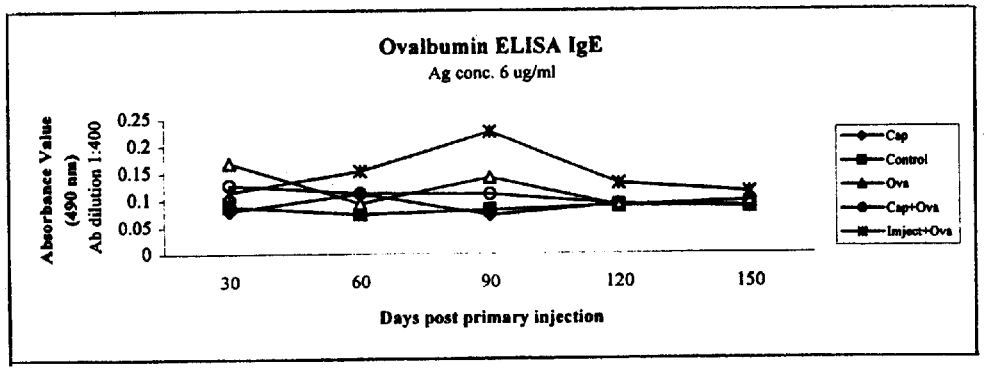

The procedures described above were carried out using HIV-1 antigen prepared from 10-119-000 (Advanced Biotechnologies, Inc.) using the protein purification procedures described in Example 2. Solutions of antigen alone (6.9 µg HIV per mouse), washed calcium phosphate/cellobiose/antigen particles (9.5 µg HIV per mouse), and antigen with Imject adjuvant (6.9 µg HIV per mouse) were each administered to 6 mice as described above, and anti-HIV antibody titer was evaluated by ELISA two weeks after primary infection. The results are presented in FIG. 6.

EXAMPLE 8

Four different antigens were combined with CAP to study its effectiveness as an adjuvant. These four antigens included Ovalbumin (Ova), Tuberculosis (TB), HSV-2 and EBV.

The Ovalbumin and Tuberculosis coated particles were prepared following the procedures of examples 1 and 4. The cellobiose coated CAP was mixed for one hour with 0.5 mg of Ovalbumin or Tuberculosis antigen. The samples were then washed three times (centrifuged at 4500 rpm for 15 minutes at 4° C.) with PBS. 1 mL of Imject-alum adjuvant was mixed with the same amount of Ovalbumin and Tuberculosis. A solution of antigen alone was prepared by mixing 0.5 mg of Ovalbumin and Tuberculosis antigen with 1 mL of PBS respectively.

The HSV-2 CAP and EBV CAP were prepared by co-crystallizing the viral protein with the CAP similar to the procedure described in Example 3. The resulting CAP with either HSV-2 or EBV dispersed therein was then subsequently treated with cellobiose and the surface coated with antigen as described above.

Six mice each were immunized by i.p. injection with one of the following antigens: Ova alone, Ova+Alum, Ova+CAP, TB alone, TB+Alum, TB+CAP, HSV-2 alone, HSV-2+Alum, HSV-2+CAP, EBV alone, EBV+Alum, EBV+CAP and CAP alone. The concentration of CAP to Alum is 1:100 for the OVA and TB vaccine constructs. The concentration of CAP to Alum is equivalent for HSV-2 and EBV vaccine constructs. All mice were immunized with a primary injection and given two or three booster injections at two-week intervals. Blood was collected and IgG, IgGI, IgG2a, and IgE antibody titers in immunized mice were measured by ELISA. The results are presented in FIGS. 8–11, which show different levels of antibodies between the different groups of immunized mice.

EXAMPLE 9

A suspension of calcium phosphate particles is prepared following the procedures of Example 1, and the particle size and presence of any endotoxin determined. Cellobiose glue is applied to the particles by suspending them in a solution of 292 mM cellobiose stock added to the suspension of calcium phosphate particles at a ratio of 1 mL of cellobiose solution to 20 mL of particle suspension. The mixture is gently mixed and allowed to stand overnight. A cDNA encoding an immunogenic polypeptide of a disease-causing pathogen is inserted into a pcDNA3 plasmid according to techniques familiar to those in the art. The coated particles are then contacted with a solution of plasmid DNA, and co-incubated at room temperature or 40° C.

EXAMPLE 10

10 mL of a 10% stock solution of PEG-3550 in water was prepared. 20 µL of this PEG stock solution was combined with 2 mL of a solution of 500 nm calcium phosphate particles prepared according to the procedure described in Example 1 and incubated for 1 hour at room temperature. The mixture was centrifuged at 4000×g for 15 minutes to remove free PEG in a supernatant fraction. The pellet of particles was resuspended in 2 mL of spent buffer left over from preparation of the CAP particles. 100 µL of human insulin (20 mg/mL) was added, and the mixture incubated for 1.5 hour at 5–10° C.

EXAMPLE 11

Six male diabetic Taconic NOD mice and 2 control mice (C57) at 12 weeks of age were checked for normal blood glucose levels and divided into groups. Three NOD mice were designated as the NOD test group, three NOD mice were designated the NOD control group, and the two C57 mice were designated the C57 control group. Feeding of all animals was stopped at least 18 hours before testing, and fasting blood samples taken and checked for glucose. Each animal was given 1 mL of 300 mg/mL glucose solution orally, and the glucose level checked one hour after glucose infusion. Each animal was anesthetized. The mouth of each animal was opened, and a blunt hypodermic needle inserted into each trachea. 50 µL of the composition prepared in Example 2 was administered through the hypodermic needle to each animal in the NOD test and C57 control groups. 50 µL of spent buffer solution from the preparation of the calcium phosphate particles was given to the NOD control group, which received no insulin. Glucose levels were checked every hour during the first six hours of treatment. A final glucose level was checked after 24 hours of treatment.

Figure 15:
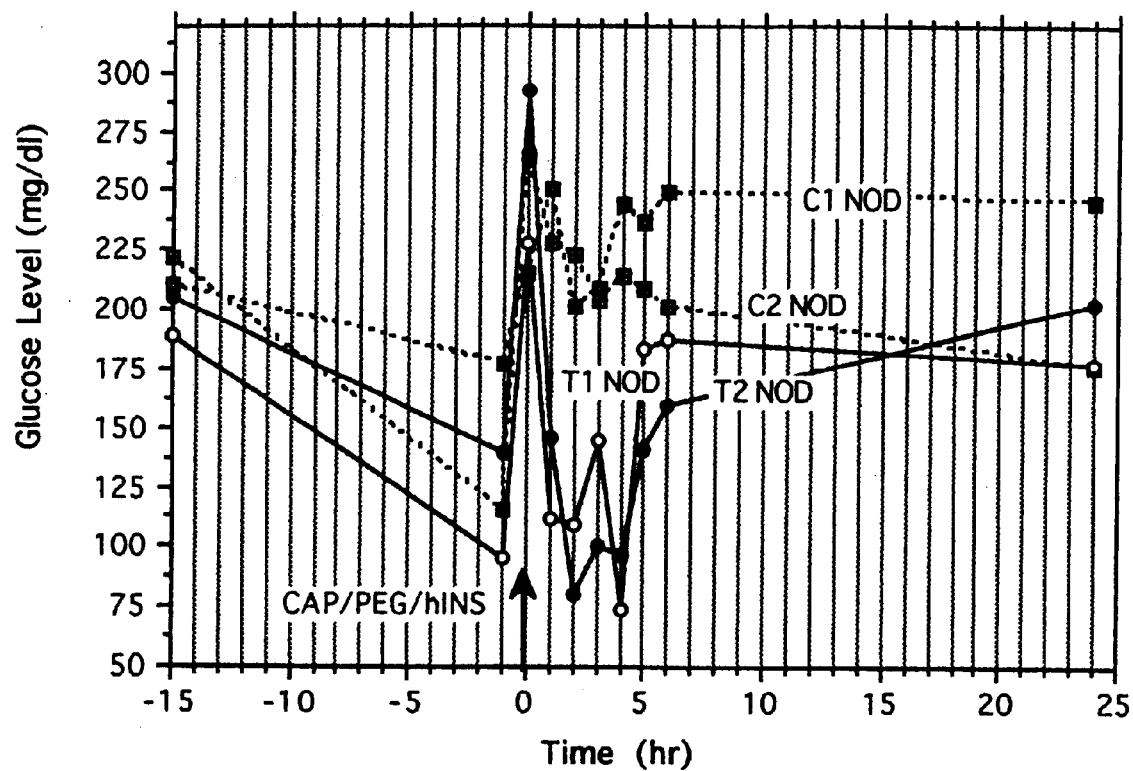

The test results are plotted in the graph shown in FIG. 15. In the graph, the data at −15 hours represents the glucose level of each mouse before fasting, and the data at −1 hours represents the glucose level of each mouse after 17 hours of fasting. The data at 0 represents the glucose level of each mouse 1 hour after glucose administration, and the data at +1 hour represents the glucose level of each mouse after 1 hour of insulin treatment. The test results show that the calcium phosphate/PEG/human insulin particles were effective in controlling glucose levels in the rat up to at least 4 hours after treatment.

EXAMPLE 12

Particles having a surface modifying agent (2), such as polyethylene glycol (PEG), impregnated within the core calcium phosphate particle (4) and having a material (6), such as a therapeutic protein or peptide, and more particularly human insulin, at least partially coated on the surface are shown in FIG. 13C. Such particles having at least a partial coating of human insulin were prepared by simultaneously injecting 5 mL of 125 mM $CaCl_2$ and 1 mL of 156 mM sodium citrate into a 250 mL beaker containing 100 mL of 1% polyethylene glycol (PEG), under constant stirring. Precipitate was formed following the addition of 5 mL of 125 mM $Na_2HPO_4$. Mixing was continued for 48 hours at room temperature. The resulting particle suspension was sonicated at maximum power for 15 minutes and stored at room temperature until ready for insulin attachment.

A therapeutic protein or peptide, such as human insulin at final 0.9 mg/mL, was incubated with batches of 20 mL PEG-entrapped particle suspension for 1 hour at room temperature by gentle mixing on a rocking platform. Finished particles were washed twice in distilled water and stored either at 4° C. (preferably not longer than 1 month) for lyophilized to dryness for future use. Illustrative particles are shown in FIG. 13C. Incorporating a surface modifying agent such as PEG in the particle structure results in increased insulin loading capacity, measured as mg bound-insulin/100 mg particle (44±4% w/w), increased insulin per particle (12.5 U/mg particle, based on recombinant insulin unit by HPLC (high-performance liquid chromatography)=28.4 U/mg protein), and increased loading efficiency of 40.0±3.6% w/w, measured by mg bound-insulin/100 mg insulin originally added during binding.

EXAMPLE 13

Particles having both a surface modifying agent (2) and a material (6), such as a therapeutic protein or peptide impregnated within the core calcium phosphate particle (4) are shown in FIG. 14. Such particles having human insulin impregnated therein were prepared by adding one mL of 20 mg/mL of human insulin into a 50 mL beaker containing 20 mL of 1% PEG and mixed thoroughly for about 1 min. Sodium citrate at 156 mM (0.2 mL) and $CaCl_2$ at 125 mM concentrations (1 mL) were injected into PEG-human insulin solution simultaneously while stirring. One mL of 125 mM $Na_2HPO_4$ was added to initiate the particle formation. Stirring was continued for 48 hours at room temperature. The resulting particle suspension was sonicated at maximum power setting for 15 minutes. Finished particles were washed twice in distilled water and kept refrigerated at 4° C. (no more than one month) or lyophilized to dryness for further use. Illustrative particles are shown in FIG. 14. The resulting formulation has an increased loading capacity, measured as mg bound-insulin/100 mg particle (77±7% w/w), increased insulin per particle (21.2 U/mg particle, based on recombinant insulin unit by HPLC (high-performance liquid chromatography)=28.4 U/mg protein), and increased loading efficiency of 89.5±8.1% w/w, measured by mg bound-insulin/100 mg insulin originally added during binding.

EXAMPLE 14

Calcium phosphate core particles of the present invention, (CAP), were tested in comparison to calcium phosphate particles manufactured by Superfos Biosector a/s, referred to as "Accurate CAP," to study the effectiveness of the CAP particles of the present invention as an adjuvant.

HSV-2 CAP was prepared by co-crystallizing the viral protein with the CAP similar to the procedure described in Example 3. The resulting CAP with HSV-2 dispersed therein was then subsequently treated with cellobiose and the surface coated with antigen as described above.

Five mice each were immunized by i.p. injection with one of the following antigens: HSV-2+CAP or HSV-2+Accurate CAP. The mice were immunized with a primary injection and given two or three booster injections at two-week intervals. Blood was collected and IgG, IgGI, and IgG2a antibody titers in immunized mice were measured by ELISA. The results are presented in FIGS. 7A–C, which show different levels of antibodies between the different groups of immunized mice. Of particular importance is the result shown in FIG. 7C. FIG. 7C shows that the IgG2a antibody titer for the CAP particles of the present invention triggered a strong IgG2a response.

The procedures described above and exemplified above can be modified by those having skill in the art to yield other embodiments of the invention. For example, the material to be dispersed throughout the particle can be co-crystallized and impregnated within the particle as described above, and the resulting particles can be coated with the same or different material, using the coating methods described above. The core particles may also have a partial coating of one or a mixture of surface modifying agents described above to help adhere material coating the particle to the surface thereof.

The present invention has been described above with respect to certain specific embodiments thereof, however it will be apparent that many modifications, variations, and equivalents thereof are also within the scope of the invention.

What is claimed is:

1. A method for preparing one or more particles of calcium phosphate having diameters between about 300 nm to about 4000 nm, comprising reacting a soluble calcium salt with a soluble phosphate salt, wherein the reacting comprises:

(a) mixing an aqueous solution of calcium chloride with an aqueous solution of sodium citrate to form a mixture, (b) adding an aqueous solution of sodium phosphate to the mixture to form a solution, (c) stirring the solution until particles of the desired size and comprising calcium phosphate are obtained.

2. The method of claim 1, wherein the concentrations of each of the aqueous calcium chloride, the aqueous sodium citrate, and the aqueous sodium phosphate solutions are independently between about 5 mM and about 100 mM.

3. The method of claim 1, further comprising adding an antigenic material along with one or more of the aqueous solutions forming the particle, to form one or more particles comprising calcium phosphate that are at least partially co-crystallized with the antigenic material.

* * * * *

UNITED STATES PATENT AND TRADEMARK OFFICE
CERTIFICATE OF CORRECTION

PATENT NO. : 6,355,271 B1
DATED : March 12, 2002
INVENTOR(S) : Steve J.D. Bell et al.

It is certified that error appears in the above-identified patent and that said Letters Patent is hereby corrected as shown below:

Title page,
Item [75], Inventor, please delete inventor "Tulin Morco" and substitute -- Tulin Morcol -- therefor Column 1,
Lines 55 and 67, delete "polynucelotide" and substitute -- polynucleotide -- therefor Column 2,
Line 35, delete "product" and substitute -- produce -- therefor
Line 58, delete "Microhiol" and substitute -- Microbial. -- therefor Column 3,
Line 21, delete "Nafl." and substitute -- Natl. -- therefor Column 6,
Line 37, delete "polynucelotide" and substitute -- polynucleotide -- therefor Column 8,
Line 46, delete first "a"

Column 13,
Line 54, delete "polynucelotide" and substitute -- polynucleotide -- therefor Column 18,
Line 2, delete "of"

UNITED STATES PATENT AND TRADEMARK OFFICE
CERTIFICATE OF CORRECTION

PATENT NO. : 6,355,271 B1
DATED : March 12, 2002
INVENTOR(S) : Steve J.D. Bell et al.

It is certified that error appears in the above-identified patent and that said Letters Patent is hereby corrected as shown below:

Column 19,
Line 40, delete "No inflamation" and substitute -- No inflammation -- therefor
Line 40, delete "Mild inflamation" and substitute -- Mild inflammation -- therefor
Line 41, delete "Severe inflamation" and substitute -- Severe inflammation -- therefor Signed and Sealed this Twenty-eighth Day of January, 2003

JAMES E. ROGAN
*Director of the United States Patent and Trademark Office*